US008244468B2

(12) United States Patent  
Scalisi et al.

(10) Patent No.: US 8,244,468 B2  
(45) Date of Patent: Aug. 14, 2012

(54) SYSTEM AND METHOD FOR CREATING AND MANAGING A PERSONALIZED WEB INTERFACE FOR MONITORING LOCATION INFORMATION ON INDIVIDUALS AND OBJECTS USING TRACKING DEVICES

(75) Inventors: Joseph F. Scalisi, Yorba Linda, CA (US); Desiree Mejia, Redondo Beach, CA (US); David M. Morse, Laguna Hills, CA (US); Michael L. Beydler, Irvine, CA (US)

(73) Assignee: Location Based Technology Inc., Irvine, CA (US)

( * ) Notice: Subject to any disclaimer, the term of this patent is extended or adjusted under 35 U.S.C. 154(b) by 1276 days.

(21) Appl. No.: 11/935,901

(22) Filed: Nov. 6, 2007

(65) Prior Publication Data

US 2009/0119119 A1   May 7, 2009

(51) Int. Cl.  
*G01C 21/10* (2006.01)

(52) U.S. Cl. ..................................... 701/519

(58) Field of Classification Search ............... 701/205, 701/207  
See application file for complete search history.

(56) References Cited

U.S. PATENT DOCUMENTS

| | | | |
|---|---|---|---|
| 3,924,102 A | 12/1975 | Hanekom | |
| 4,218,582 A | 8/1980 | Hellman et al. | |
| 4,850,007 A | 7/1989 | Marino et al. | |
| 5,079,541 A | 1/1992 | Moody | |
| 5,127,042 A | 6/1992 | Gillig et al. | |
| 5,353,331 A | 10/1994 | Emery et al. | |
| 5,386,468 A | 1/1995 | Akiyama et al. | |
| 5,432,542 A | 7/1995 | Thibadeau et al. | |
| 5,541,976 A | 7/1996 | Ghisler | |
| 5,555,286 A | 9/1996 | Tendler | |
| 5,565,909 A | 10/1996 | Thibadeau et al. | |
| 5,785,181 A | 7/1998 | Quartararo, Jr. | |
| 5,876,765 A | 3/1999 | Hinterlechner et al. | |
| 5,967,841 A | 10/1999 | Bianca et al. | |
| 5,973,599 A | 10/1999 | Nicholson et al. | |
| 6,088,453 A | 7/2000 | Shimbo | |
| 6,141,356 A | 10/2000 | Gorman | |
| 6,236,365 B1 | 5/2001 | LeBlanc et al. | |
| 6,243,039 B1 * | 6/2001 | Elliot | 342/457 |
| 6,278,370 B1 * | 8/2001 | Underwood | 340/573.1 |

(Continued)

FOREIGN PATENT DOCUMENTS

JP         10325735         12/1998

(Continued)

OTHER PUBLICATIONS

Huff, Greg H., et al., "Directional Reconfigurable Antennas on Laptop Computers: Simulation, Measurement and Evaluation of Candidate Integration Positions", *IEEE Transactions on Antenaas*, vol. 52, No. 12 (Dec. 2004),pp. 3220-3227.

(Continued)

*Primary Examiner* — Husseinn A. Elchanti

(57) ABSTRACT

A personalized format webpage is generated to monitor location information. A management dashboard module is disclosed to provide a user access to location information of a tracking device associated with an object or an individual. An account services module provides menu options to the user. A wizard menu enables the user to enter billing information, identification settings of the tracking device, and coverage zones. Alert messages associated with the tracking device are generated in accordance with selected coverage zones and provided to the user.

22 Claims, 28 Drawing Sheets

U.S. PATENT DOCUMENTS

| | | | |
|---|---|---|---|
| 6,300,875 B1* | 10/2001 | Schafer | 340/573.1 |
| 6,327,533 B1* | 12/2001 | Chou | 701/207 |
| 6,388,612 B1 | 5/2002 | Neher | |
| 6,414,629 B1 | 7/2002 | Curcio | |
| 6,441,741 B1 | 8/2002 | Yoakum | |
| 6,445,921 B1 | 9/2002 | Bell | |
| 6,453,037 B1 | 9/2002 | Welter, Jr. | |
| 6,498,797 B1 | 12/2002 | Anerousis et al. | |
| 6,546,253 B1 | 4/2003 | Chow et al. | |
| 6,611,755 B1 | 8/2003 | Coffee et al. | |
| 6,633,835 B1 | 10/2003 | Moran et al. | |
| 6,654,883 B1 | 11/2003 | Tatebayashi | |
| 6,674,368 B2 | 1/2004 | Hawkins et al. | |
| 6,708,028 B1 | 3/2004 | Byrne | |
| 6,716,101 B1* | 4/2004 | Meadows et al. | 455/456.1 |
| 6,732,090 B2 | 5/2004 | Shanahan et al. | |
| 6,735,630 B1 | 5/2004 | Gelvin et al. | |
| 6,747,561 B1 | 6/2004 | Reeves et al. | |
| 6,754,470 B2 | 6/2004 | Hendrickson et al. | |
| 6,768,942 B1 | 7/2004 | Chojnacki | |
| 6,778,089 B2 | 8/2004 | Yoakum | |
| 6,812,824 B1 | 11/2004 | Goldinger et al. | |
| 6,819,247 B2 | 11/2004 | Birnbach et al. | |
| 6,833,787 B1 | 12/2004 | Levi | |
| 6,850,252 B1 | 2/2005 | Hoffberg | |
| 6,859,533 B1 | 2/2005 | Wang et al. | |
| 6,879,244 B1 | 4/2005 | Scalisi | |
| 6,882,897 B1 | 4/2005 | Fernandez | |
| 6,928,280 B1 | 8/2005 | Xanthos et al. | |
| 6,937,726 B1 | 8/2005 | Wang | |
| 6,952,181 B2 | 10/2005 | Karr et al. | |
| 6,975,941 B1 | 12/2005 | Lau et al. | |
| 6,978,021 B1 | 12/2005 | Chojnacki | |
| 6,988,026 B2 | 1/2006 | Breed | |
| 6,992,584 B2 | 1/2006 | Dooley et al. | |
| 6,998,985 B2 | 2/2006 | Reisman et al. | |
| 6,998,995 B2 | 2/2006 | Nakajima | |
| 7,020,701 B1 | 3/2006 | Gelvin et al. | |
| 7,038,590 B2 | 5/2006 | Hoffman et al. | |
| 7,049,957 B2 | 5/2006 | Watson | |
| 7,064,711 B2 | 6/2006 | Strickland et al. | |
| 7,065,244 B2 | 6/2006 | Akimov | |
| 7,065,348 B1 | 6/2006 | Aoki et al. | |
| 7,065,370 B2 | 6/2006 | Ogaki et al. | |
| 7,079,650 B1 | 7/2006 | Knudsen | |
| 7,088,242 B2 | 8/2006 | Aupperle et al. | |
| 7,088,252 B2 | 8/2006 | Weekes | |
| 7,099,921 B1* | 8/2006 | Engstrom et al. | 709/206 |
| 7,109,868 B2 | 9/2006 | Yoakum | |
| 7,119,669 B2 | 10/2006 | Lundsgaard et al. | |
| 7,120,928 B2 | 10/2006 | Sheth et al. | |
| 7,139,396 B2 | 11/2006 | Montgomery et al. | |
| 7,146,367 B2 | 12/2006 | Shutt | |
| 7,149,189 B2 | 12/2006 | Huntington et al. | |
| 7,155,238 B2 | 12/2006 | Katz | |
| 7,158,912 B2 | 1/2007 | Vock et al. | |
| 7,181,192 B2 | 2/2007 | Panasik et al. | |
| 7,200,673 B1 | 4/2007 | Augart | |
| 7,218,242 B2 | 5/2007 | Scalisi et al. | |
| 7,246,007 B2 | 7/2007 | Ferman et al. | |
| 7,257,836 B1 | 8/2007 | Moore | |
| 7,268,700 B1 | 9/2007 | Hoffberg | |
| 7,272,212 B2 | 9/2007 | Eberle et al. | |
| 7,272,662 B2 | 9/2007 | Chesnais et al. | |
| 7,284,191 B2 | 10/2007 | Grefenstette et al. | |
| 7,299,277 B1 | 11/2007 | Moran et al. | |
| 7,302,634 B2 | 11/2007 | Lucovsky et al. | |
| 7,313,825 B2 | 12/2007 | Redlich et al. | |
| 7,501,952 B2 | 3/2009 | Forster | |
| 7,501,984 B2 | 3/2009 | Forster et al. | |
| 7,598,855 B2 | 10/2009 | Scalisi | |
| 7,612,663 B2 | 11/2009 | Sun | |
| 7,626,499 B2 | 12/2009 | Burneske et al. | |
| 7,728,724 B1 | 6/2010 | Scalisi et al. | |
| 7,995,994 B2 | 8/2011 | Khetawat et al. | |
| 2001/0030667 A1 | 10/2001 | Kelts | |
| 2001/0048364 A1 | 12/2001 | Kalthoff et al. | |
| 2002/0041328 A1 | 4/2002 | LeCompte et al. | |
| 2002/0067256 A1 | 6/2002 | Kail, IV | |
| 2002/0077130 A1 | 6/2002 | Owensby | |
| 2002/0180602 A1 | 12/2002 | Yoakum | |
| 2002/0186135 A1 | 12/2002 | Wagner | |
| 2002/0196123 A1 | 12/2002 | Diehl et al. | |
| 2003/0043200 A1 | 3/2003 | Faieta et al. | |
| 2003/0131073 A1 | 7/2003 | Lucovsky et al. | |
| 2003/0177094 A1 | 9/2003 | Needham et al. | |
| 2003/0208518 A1 | 11/2003 | Gura et al. | |
| 2003/0210262 A1 | 11/2003 | Gahm et al. | |
| 2003/0212729 A1 | 11/2003 | Eberle et al. | |
| 2003/0235307 A1 | 12/2003 | Miyamoto | |
| 2004/0010689 A1 | 1/2004 | Vanstone et al. | |
| 2004/0021573 A1 | 2/2004 | Hoffman et al. | |
| 2004/0165726 A1 | 8/2004 | Yamamichi et al. | |
| 2004/0166879 A1 | 8/2004 | Meadows et al. | |
| 2004/0172403 A1 | 9/2004 | Steele et al. | |
| 2004/0212493 A1 | 10/2004 | Stilp | |
| 2005/0012620 A1 | 1/2005 | Yoakum | |
| 2005/0024201 A1 | 2/2005 | Culpepper et al. | |
| 2005/0044356 A1 | 2/2005 | Srivastava et al. | |
| 2005/0071282 A1 | 3/2005 | Lu et al. | |
| 2005/0071736 A1 | 3/2005 | Schneider et al. | |
| 2005/0099303 A1 | 5/2005 | Suckerman | |
| 2005/0145688 A1 | 7/2005 | Milenkovic et al. | |
| 2005/0159883 A1 | 7/2005 | Humphries et al. | |
| 2005/0181870 A1 | 8/2005 | Nguyen et al. | |
| 2005/0188403 A1 | 8/2005 | Kotzin | |
| 2005/0210260 A1 | 9/2005 | Venkatesan et al. | |
| 2005/0246647 A1 | 11/2005 | Beam et al. | |
| 2005/0248459 A1 | 11/2005 | Bonalle et al. | |
| 2006/0009152 A1 | 1/2006 | Millard et al. | |
| 2006/0084420 A1 | 4/2006 | Smith et al. | |
| 2006/0205416 A1 | 9/2006 | Kayzar et al. | |
| 2006/0206246 A1 | 9/2006 | Walker | |
| 2006/0211405 A1 | 9/2006 | Scalisi et al. | |
| 2006/0232429 A1 | 10/2006 | Gonzalez | |
| 2006/0232449 A1 | 10/2006 | Jain et al. | |
| 2006/0253590 A1 | 11/2006 | Nagy et al. | |
| 2006/0290497 A1 | 12/2006 | Sugata | |
| 2007/0028088 A1 | 2/2007 | Bayrak et al. | |
| 2007/0033531 A1 | 2/2007 | Marsh | |
| 2007/0053513 A1 | 3/2007 | Hoffberg | |
| 2007/0054530 A1 | 3/2007 | Bauer et al. | |
| 2007/0061303 A1 | 3/2007 | Ramer et al. | |
| 2007/0073719 A1 | 3/2007 | Ramer et al. | |
| 2007/0083819 A1 | 4/2007 | Shoemaker | |
| 2007/0159322 A1 | 7/2007 | Garratt Campbell | |
| 2007/0229350 A1 | 10/2007 | Scalisi et al. | |
| 2007/0255620 A1 | 11/2007 | Tumminaro et al. | |
| 2007/0287473 A1 | 12/2007 | Dupray | |
| 2007/0288427 A1 | 12/2007 | Ramer et al. | |
| 2008/0010585 A1 | 1/2008 | Schneider et al. | |
| 2008/0028063 A1 | 1/2008 | Holmes et al. | |
| 2008/0059504 A1 | 3/2008 | Barbetta et al. | |
| 2008/0059889 A1 | 3/2008 | Parker et al. | |
| 2008/0088437 A1 | 4/2008 | Aninye et al. | |
| 2008/0090550 A1 | 4/2008 | Scalisi et al. | |
| 2008/0108370 A1* | 5/2008 | Aninye | 455/456.1 |
| 2008/0109762 A1 | 5/2008 | Hundal et al. | |
| 2008/0129491 A1 | 6/2008 | Ruperto et al. | |
| 2008/0171559 A1 | 7/2008 | Frank et al. | |
| 2008/0172173 A1 | 7/2008 | Chang et al. | |
| 2008/0228654 A1 | 9/2008 | Edge | |
| 2008/0252254 A1 | 10/2008 | Osada | |
| 2008/0252459 A1 | 10/2008 | Butler et al. | |
| 2009/0098857 A1 | 4/2009 | De Atley | |
| 2009/0098903 A1 | 4/2009 | Donaldson et al. | |
| 2009/0103722 A1 | 4/2009 | Anderson et al. | |
| 2009/0111393 A1 | 4/2009 | Scalisi et al. | |
| 2009/0117921 A1 | 5/2009 | Beydler et al. | |
| 2009/0174603 A1 | 7/2009 | Scalisi et al. | |
| 2009/0177385 A1 | 7/2009 | Matas et al. | |
| 2009/0189807 A1 | 7/2009 | Scalisi et al. | |
| 2009/0315706 A1 | 12/2009 | Scalisi et al. | |
| 2009/0315767 A1 | 12/2009 | Scalisi et al. | |
| 2012/0086571 A1 | 4/2012 | Scalisi et al. | |
| 2012/0089492 A1 | 4/2012 | Scalisi et al. | |

FOREIGN PATENT DOCUMENTS

| | | |
|---|---|---|
| JP | 11064480 | 3/1999 |
| JP | 13074494 | 3/2001 |
| KR | 1020020001257 | 1/2002 |
| KR | 1020050063802 | 6/2005 |
| KR | 1005322589 | 11/2005 |
| WO | WO-2007107022 | 9/2007 |

OTHER PUBLICATIONS

Fredrick, Jonathan D., et al., "Smart Antennas Based on Spatial Multiplexing of Local Elements (SMILE) for Mutual Coupling Reduction" *IEEE Transactions on Antennas and Propagation*, vol. 52, No. 1, (Jan. 2004),pp. 106-114.

"Electric Vehicle (EV) Charging Information" *Pasadena Water & Power Website*, www.cityofpasadena.net.

"Mobile Transmit Diversity", *Magnilia Broadband Internet Article*, 14 pages.

Hansen, Michael "Overmolding: A Multifaceted Medical Device Technology", *Medical Device & Diagnostic Industry*, Jan. 2006 ,5 pages.

"Material Property Data for Various Thermoplastic Elastomers", *MATLAB*, (May 29, 2007),7 pages.

Mannion, Patrick "Antenna Diversity Doubles CDMA Net Capacity", *EE Times*, (May 12, 2003),3 pages.

Burk, Steve "Overmolding of Embedded Electronics", *Connector Specifier*, Retrieved from the Internet at http:/cs.pennet.com on May 20, 2007,(Apr. 2001),4 pages.

Schuster, Mike et al., "Increasing the Frequency Response of the ADXL Series Accelerometers", *Analog Devices Application Note AN-377*, (Feb. 2006),1 page.

"Small and Thin +_5g Accelerometer", *Analog Devices—ADXL320*, (2004),16 pages.

Matsakis, Demetrios "The Timing Group Delay (TGD) Correction and GPS Timing Basis", *Proceedings of the 63rd Annual Meeting of the Institute of Navigation*, Cambridge, MA, (Apr. 2007),6 pages.

"GPS Compass Solutions—Application vs. Accuracy", *CEACT Information Systems*, (Sep. 13, 2006),10 pages.

"ET301 GPS-UAV Developement Platform", (Jul. 12, 2006),11 pages.

Lemaire, Christophe "Surface Micromachined Sensors for Vehicle Navigation Systems", *Analog Devices, Inc.*, Retrieved from the Internet from http://www.analog.com/en/content/0,2886,764%255F800%255F8077%255F0,00.html on Dec. 25, 2007.,4 pages.

Li, Xiaojing et al., "The Complementary Characteristics of GPS and Accelerometer in Monitoring Structural Deformation" *ION 2005 Meeting*, (2005),9 pages.

Li, Xiaojing et al., "Full-Scale Structural Monitoring Using an Integrated GPS and Accelerometer System", *University of New South Wales*, (Feb. 14, 2006),15 pages.

\* cited by examiner

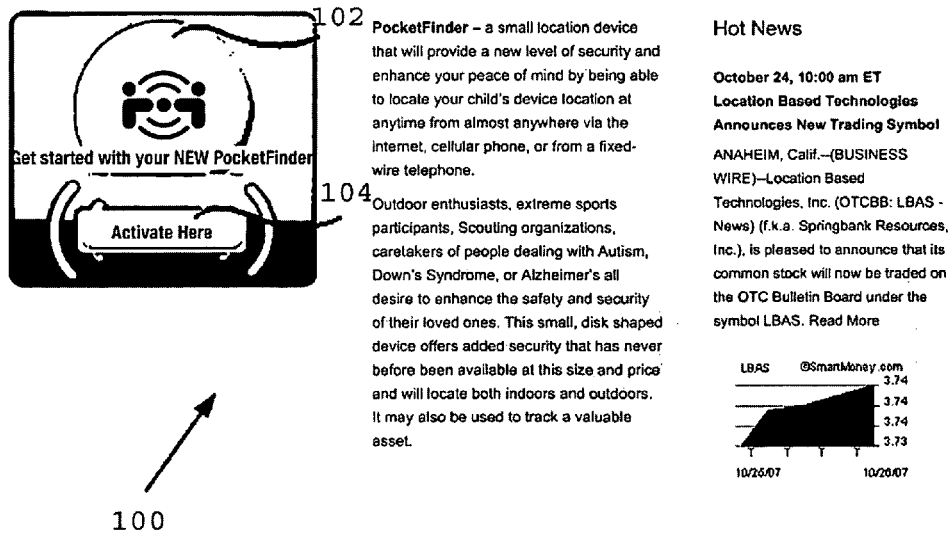
Figure 1 pocketfinder Product Activation — 104

1. Let's get started!  2. New Account  3. Service Plan  4. Device Setup  5. Finish First Name Last Name Address Address 2

Zip Code:   State
            California

Home Phone

Mobile (Cell) Phone

Note: Your mobile phone will need to be verified in your my account settings once you've completed activation before it can be used as a notification method.

[next]

Site Credit   Privacy Policy   Terms and Conditions   © 2007 PocketFinder. All Rights Reserved

Figure 2B

| | Premium $20/month* | Standard $10/month* |
|---|---|---|
| Number of location lookups | Unlimited | 100/month |
| Number of emergency contacts | Unlimited | 20 |
| Email Alerts | ✓ | ✓ |
| SMS Alerts | ✓ | ✓ |
| Voice Phone Alerts | ✓ | |
| Touch-Tone phone location lookups | ✓ | |
| Some other cool feature | ✓ | |
| This is the must have feature | ✓ | |
| *based on a 1 year billing interval | select | select | pocketfinder — Product Activation — 104

(1) Let's get started! (2) New Account (3) Service Plan (4) Device Setup (5) Finish Site Credit   Privacy Policy   Terms and Conditions   © 2007 PocketFinder. All Rights Reserved

| Locate by Phone - Call 972-331-1793 | Friday, October 26, 2007 5:11 PM   Home   Log Out |

Dashboard          Limited Users                              My Account

Account Settings

Account Holder Information ~~~ 114

☐ Allow Editing

| First Name: | Address 1: | Your username must be 6 characters or more in length and your password must be numerical. |
|---|---|---|
| John | 4999 E. La Palma Ave. | Current Username: |
| Last Name: | Address 2: | |
| Smith | | |
| Email: | City: | Password: |
| Mike@actti.com  VALID | Anaheim | |
| Home Phone: | State: | Confirm Password: |
| 8006150898 | California | |
| Mobile Phone: | Zip: | |
| 9499105698  VERIFY | 92807 | |

SAVE

Contact Book ~~~ 116

Help Settings ~~~ 118

Account Billing ~~~ 120

Cancelling your Account ~~~ 122

Leave a comment or report a bug.   Site Credit   Privacy Policy   Terms and Conditions   © 2007 PocketFinder. All Rights Reserved

| Locate by Phone - Call 972-331-1793 | Friday, October 26, 2007 5:12 PM | Home | Log Out |

Dashboard    Limited Users                                My Account

Little Dave ⌒‾‾134

Identification Settings

Select an icon for your device.

General Device Information

Medical Profile ⌒‾‾152

Medical data for this device are optional and store with the utmost security. This information at your request may be forward electronically to provide medical and local law enforcement agencies with the information they need to assist in emergency situations.

Front Head Photo

Definition: Default
Size (px): 400 x 400  (jpg - 23.46 KBytes)    Browse...

Full Body Photo

No image selected    Browse...

Birthday: Ex. 03/24/1981
`7/1/2001`

Allergic Medications:
`Ciclor and penicillin.`

Physician's Name:

Blood Type:
`O+`

Physician's Phone Primary Number

Medical Conditions:
`Bee stings.`
`Asthmatic.`

SAVE

Missing Persons

Leave a comment or report a bug.   Site Credit   Privacy Policy   Terms and Conditions   © 2007 PocketFinder. All Rights Reserved

Figure 8

| Locate by Phone - Call 972-331-1793 | | Friday, October 26, 2007 5:18 PM | Home | Log Out |

| | Dashboard | Limited Users | | My Account |

Account Settings

Account Holder Information

Contact Book ⌒ 116 add a new contact

| First Name | Last Name | Home Phone | Mobile Phone | | Email | | | | |
|---|---|---|---|---|---|---|---|---|---|
| Josh | Dahlhauser | 3103067626 | 8186874360 | VALID | josh.dahlhauser@gmail.com | VALID | ☑ | ▮ | 166 |
| Mike | Beydler | | 7143500743 | VALID | mike@actti.com | VERIFY | ☑ | ▮ | |

Help Settings

Account Billing

Cancelling your Account

Leave a comment or report a bug.  Site Credit  Privacy Policy  Terms and Conditions  © 2007 PocketFinder. All Rights Reserved

Figure 11

Locate by Phone - Call 972-331-1793   Friday, October 26, 2007 5:19 PM   Home   Log Out Dashboard   Limited Users   My Account

Limited Access Users

Create Limited Access User accounts for your devices. Limited Access User accounts allows you to create temporary accounts so someone you trust can view and track the location of this device. Limited Access User accounts are limited to locating only.

User Account Information

First Name:

Last Name:

Email Address:

Phone Number:

Username:

Password:

Password(Confirm):

[ Add User ]

Assigned to the following devices:

The newly created user will be able to see the location for the following checked devices. Don't worry access can always be modified anytime by you.

☐ Little Dave — 172
☐ Mom
☐ Dad
☐ Spaz

Active User Accounts

— 174

| First Name | Last Name | Username | Little Dave | Mom | Dad | Spaz | |
|---|---|---|---|---|---|---|---|
| 1234 | 1234 | 1234 | ☑ | ☑ | ☑ | ☑ | delete |
| Derek | Unger | 8188 | ☐ | ☑ | ☑ | ☐ | delete |

[ SAVE ]

Leave a comment or report a bug.   Site Credit   Privacy Policy   Terms and Conditions   © 2007 PocketFinder. All Rights Reserved

| Locate by Phone - Call 972-331-1793 | Friday, October 26, 2007 5:32 PM    Home    Log Out |

Dashboard     Limited Users                   My Account

 Little Dave

Identification Settings

Select an icon for your device.

General Device Information

Medical Profile                                                             280

Missing Persons — 278

Please make sure the follow information is up-to-date and complete before printing    [ Print Missing Flyer ]

Location last seen
Santa Ana Frwy
Irvine, United States 92618
[ Get Last Location ]

Last seen wearing
Blue and white Baseball shirt

Date of disappearance
7/1/07

Age
6

Wears Glasses
N

Hearing Impaired
N

Gender
-

Race
White

Height
3' 8"

Weight
65

Hair color
Blond

Police Department
MS

Police Officer
Rick Ave

Phone
744-544-3377

Case #
None

Eye color
Blue

Nicknames
Dave

Birthmarks
None

Scars
None

[ SAVE ]

Figure 20

Locate by Phone - Call 972-331-1793

MISSING PERSON

 

Location Last Seen: Santa Ana Frwy Irvine, United States 92618
Last Seen Wearing: Blue and white Baseball shirt
Last Seen On: 7/1/07

Description:
Name: Dave Smith
Nicknames: Little Dave
Age: 6
Gender:
Race: White
Height: 3' 8"
Weight: 65
Hair Color: Blond
Wears Glasses: N
Eye Color: Blue
Hearing Impaired: N
Birthmarks: None
Scars: None

280

Doctor Contact Information:
Physician's Contact:
Dr. Thomson
7154454445
Medical Issues:
Notes: Bee stings. Asthmatic.

If you have any information that may help lead to the whereabouts of this person please contact:
Police Department: MS
Police Officer: Rick Ave
Phone: 744-544-3377
Case No.: None

Figure 21

SYSTEM AND METHOD FOR CREATING AND MANAGING A PERSONALIZED WEB INTERFACE FOR MONITORING LOCATION INFORMATION ON INDIVIDUALS AND OBJECTS USING TRACKING DEVICES

RELATED APPLICATION

This application incorporates by reference U.S. patent application Ser. No. 11/753,979 filed on May 25, 2007, entitled "Apparatus and Method for Locating Individuals and Objects using Tracking Devices."

BACKGROUND OF THE INVENTION

1. Field of the Invention

The invention relates generally to a system and method for creation and deployment of personalized, dynamic web services to access location information on individuals and objects. More particularly, the present invention relates in one embodiment to a system for creation of a personalized, dynamic, web-interface that accesses location information of a tracking unit associated with an individual or object that uses wireless data transfer and/or wireless location and tracking systems and wireless communication system (WCS).

2. Description of Related Technology

In conventional communication systems, location information of individuals may be monitored. For instance, location information such as positional coordinates may be tracked or monitored for a variety of individuals, such as children, Alzheimer's syndrome patients, or mentally ill persons. Furthermore, location information for animals, such as cats and dogs, may be tracked using these conventional systems to locate a lost or stolen animal. In other conventional communication systems, scientists, such as zoologists, track, for example, wild animals to study and collect data related to their mating and/or nocturnal behavioral patterns.

In addition, objects are also tracked or located that use these systems. For example, merchants choose to track the location of goods as part of an inventory function and/or an anti-theft mode. In another example, police often use location-tracking systems to facilitate recovery of stolen automobiles, such as the LoJack™ vehicle recovery system offered by the LoJack Corporation of Westwood, Mass., in the United States. Automobile rental agencies often track a location of automobiles that customers rent to ensure their automobile is maintained within a contracted rental use boundary. Other location systems provided in select automobiles assist a driver navigating to a desired destination, such as the OnStar™ system offered by the OnStar Corporation of Detroit, Mich., in the United States.

Global Positioning System (GPS) technology may be incorporated in these conventional communication systems. GPS technology determines positional information of a GPS receiver based on measuring signal transfer times between satellites having known positions and the GPS receiver. The signal transfer time of a signal is proportional to a distance of a respective satellite from the GPS receiver. Consequently, the distance between the satellite and the GPS receiver can be converted, utilizing signal propagation velocity, into a respective signal transfer time. The positional information of the GPS receiver is calculated based on distance calculations from at least four satellites.

As such, GPS technology provides outdoor, line-of-sight communication between a GPS receiver and a centralized station within areas that are unobstructed by fabricated structures and natural features. Fabricated structures may include multi-story buildings, bridges, dams, and the like. Natural features include mountains, hills, valleys, canyons, cliffs, and the like. Exemplary products, such as Wherifone™ and Guardian Lion™, use GPS technology to track individuals and/or objects from a centralized monitoring station.

Conventional centralized monitoring station in many instances use a map that may be two dimensional, or even a three-dimensional, topological map that depicts landscaping, marine, or other environments. The map typically displays representative icons of individuals and/or objects being tracked. In one example, a mobile device may display the three-dimensional map, including primary regions and sub-regions that are pre-programmed to create a series of overlay maps for viewing on a computer display. In yet another example, map information of a first and second user terminal is synthesized; a map is chosen based on the map information from the database; and the map information is displayed on at least one of the first user and the second user terminal. In another GPS conventional communication example, GPS positioning information is transmitted from a GPS unit and between peripheral devices, such as between a camera and a Palm Pilot, through a local wireless communication unit or interface.

In yet another example, a location of small wireless devices on roaming objects is determined by achieving ad-hoc short range wireless connectivity between the wireless devices and communication devices such as Bluetooth enabled mobile phones that pass by, where the communication devices can be located by other means, such as GPS or network-based technologies. Other examples include a location-determining device monitors at least one automatic sensor associated with a subject. Still other alert systems include upon a child feeling endangered, a panic button is pressed to send a panic signal to tell others their location. Still another conventional system depicts a personal security device that includes a manager initiating transmission of a signal to the monitoring network when a sensor senses that the transmitter has been removed from a user. Other conventional tracking and location systems include a central monitoring station utilizing software agents to analyze information received from remote tags, and to determine an appropriate action to take with respect to that information.

According to various patent prior art disclosing systems such as GPS signaling, graphics, and displays associated with user interfaces, which are described below and herein incorporated by reference. Systems generally representative of the patent prior art include: U.S. Pat. No. 7,064,711 to Strickland et al. entitled "Method for Iterative Determination of Distance between Receiving Station and Transmitting Station and Also Calculating Unit and Computer Software Product" that issued Jun. 20, 2006; U.S. Pat. No. 7,065,244 to Akimov entitled "Method for Mapping a Three Dimensional Area" that issued Jun. 20, 2006; and U.S. Pat. No. 7,065,370 to Ogaki et al. entitled "Positioning Information Transmitting Device and Positioning Information Transmitting/Receiving System" that issued on Jun. 20, 2006. Other representative prior art patents describing still other GPS apparatus and methodology include: U.S. Pat. No. 7,065,348 to Aoki entitled "Communication System for Providing Information on Position of Communication Party" issued on Jun. 20, 2006; U.S. Pat. No. 7,155,238 to Katz entitled "Wireless Location Determining Device" that issued on Dec. 26, 2006; U.S. Pat. No. 7,049,957 to Watson entitled "Local Area Positioning System" that issued on May 23, 2006, and U.S. Pat. No. 6,674,368 to Hawkins et al. entitled "Automated Tracking System" that issued on Jan. 6, 2004. Still other representative prior art patents and patent applications demonstrating additional elements of GPS systems include U.S. Pat. No. 6,998,995 to Nakajima entitled "Elevator Remote Monitoring Apparatus" that issued on Feb. 14, 2006; U.S. Pat. No. 7,038,590 to Hoffman et al. entitled "Personal Security and Tracking System" that issued on May 2, 2006; U.S. Pat. No. 7,088,252 to Weekes entitled "Systems and Apparatus for Personal Security" that issued on Aug. 8, 2006; US 2006/0232449 to Gonzalez entitled "Child Alert System" that published on Oct. 19, 2006; US 2002/0067256 to Kail IV entitled "Reprogrammable Remote Sensor Monitoring System" that published on Jun. 6, 2002; and U.S. Pat. No. 7,149,189 to Huntington et al. entitled "Network Data Retrieval and Filter Systems and Methods" that issued on Dec. 12, 2006. Most recently, still other representative prior art patents involving personalized services include U.S. Pat. No. 7,272,212 to Eberle et al. entitled "System and Method for the Creation and Automatic Deployment of Personalized, Dynamic and Interactive Voice Services" that issued on Sep. 18, 2007, illustrating a system and method for combining personalized information broadcast technology with an active voice page.

In summary, the prior art provides a user limited flexibility to adjust a controlled monitoring area about an object. In addition, the prior art provides limited flexibility for a user choosing and creating custom maps for viewing and locating objects. Furthermore, the prior art has limited ability calculating positional data of objects when GPS signaling is unavailable.

Thus, what is needed are apparatus and methods for wireless data transfer and/or wireless location and tracking systems that provide additional advantages over conventional systems. These advantages would include, inter alia, calculating positional data and location coordinates of tracking devices when GPS signaling is unavailable, providing graphical displays for subscribers which aid monitoring and tracking objects and/or individuals, and/or providing security measures when monitoring tracking devices to prevent unauthorized detection and spying on individuals.

SUMMARY OF THE INVENTION

In a first aspect of the present invention, a method is disclosed for providing location information of an object or individual to a subscriber on a webpage in a personalized format. The method includes the steps of providing a logon entry display to a user on the webpage; the display prevents keypad entries being recorded or stored with anti-key logger technology, and provides user access to a location management dashboard module in response to detecting a successful user logon. In one embodiment, the location management dashboard module includes a listing of one or more groups of tracking devices a user is capable of monitoring associated location coordinate information. Other method steps include providing an account services module in response to detecting the successful user login, the account services module comprising menu options in the personalized format to the user. In one variant, the menu options include a XML format document having a wizard menu enabling the user to navigate and enter billing information, identification settings of one or more tracking devices, and log contact information in a contact book to contact individuals. In another embodiment, the method may include the step of providing one or more alert messages associated with one or more groups of tracking devices in response to detecting a successful user login.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

BRIEF DESCRIPTION OF THE DRAWINGS

FIG. 1 is a Location and Tracking Service Webpage in accordance with an embodiment of the present invention.

FIG. 2B illustrates a Product Activation Webpage to enter New Account information (which will be verified before using as a notification method) in accordance with an embodiment of the present invention.

FIG. 2C illustrates a Product Activation Webpage to choose a service plan in accordance with an embodiment of the present invention.

FIG. 2E illustrates a Product Activation Webpage to enter payment information in accordance with an embodiment of the present invention.

FIG. 5 illustrates an Account Holder Information Webpage in accordance with an embodiment of the present invention.

FIG. 8 illustrates a Medical Profile Webpage to input Medical Data for Little Dave in accordance with an embodiment of the present invention.

FIG. 11 illustrates a Contact Book Webpage in accordance with an embodiment of the present invention.

FIG. 12 illustrates a Limited Access Users Webpage in accordance with an embodiment of the present invention.

FIG. 15 illustrates a Location Management Dashboard Webpage, Alert System Module, and Acknowledge System Module associated with the Family Members represented by Icons of Little Dave, Mom, Dad, and Spaz in accordance with an embodiment the present invention.

FIG. 16 illustrates a Location Management Dashboard Webpage associated with Mom including Location Coordinates, Battery Management Module, and Velocity Display Module in accordance with an embodiment of the present invention.

FIG. 20 illustrates Missing Persons Webpage information associated with Little Dave in accordance with an embodiment of the present invention.

FIG. 21 illustrates a Missing Person Flyer associated with Little Dave in FIG. 9 in accordance with an embodiment of the present invention.

DETAILED DESCRIPTION

Figure 2A:
FIG. 2A illustrates a Product Activation Webpage to enter a device identification code in accordance with an embodiment of the present invention.

Reference is now made to the drawings wherein like numerals refer to like parts throughout.

As used herein, the terms "location coordinates" refer without limitation to any set or partial set of integer, real and/or complex location data or information such as longitudinal, latitudinal, and elevational positional coordinates.

As used herein, the terms "tracking device" refers to without limitation to any integrated circuit (IC), chip, chip set, system-on-a-chip, microwave integrated circuit (MIC), Monolithic Microwave Integrated Circuit (MMIC), low noise amplifier, power amplifier, transceiver, receiver, transmitter and Application Specific Integrated Circuit (ASIC) that may be constructed and/or fabricated. The chip or IC may be constructed ("fabricated") on a small rectangle (a "die") cut from, for example, a Silicon (or special applications, Sapphire), Gallium Arsenide, or Indium Phosphide wafer. The IC may be classified, for example, into analogue, digital, or hybrid (both analogue and digital on the same chip and/or analog-to-digital converter). Digital integrated circuits may contain anything from one to millions of logic gates, invertors, and, or, nand, and nor gates, flipflops, multiplexors, etc. on a few square millimeters. The small size of these circuits allows high speed, low power dissipation, and reduced manufacturing cost compared with board-level integration.

As used herein, the terms "wireless data transfer", "wireless tracking and location system", "positioning system," or "wireless positioning system" refers to without limitation to any wireless system that transfers and/or determines location coordinates using one or more devices, such as Global Positioning System (GPS). The terms "Global Positioning System" refer to without limitation any services, methods, or devices that utilize GPS technology that determine a position of a GPS receiver based on measuring signal transfer times between satellites having known positions and the GPS receiver. The signal transfer time for a signal is proportional to a distance of the respective satellite from the GPS receiver. The distance between the satellite and the GPS receiver may be converted, utilizing signal propagation velocity, into the respective signal transfer time. The positional information of the GPS receiver is calculated based on distance calculations from at least four satellites.

As used herein, the terms "AGPS", "Assisted GPS", or "A-GPS", refers to without limitation any services, methods, or devices that utilizes an assistance server to help reduce required time to determine a location using GPS (such as in urban areas, when the user is located in "urban canyons", under heavy tree cover, or even indoors.) The development of AGPS is fuelled, in part, by the U.S. Federal Communications Commission's E911 to have location coordinates of a mobile device available to emergency call dispatchers. In A-GPS networks, the receiver, has limited processing power and normally under less than ideal locations for position fixing, and communicates with the assistance server that has high processing power and access to a reference network. Since the A-GPS receiver and the Assistance Server share tasks, it provides a capability to provide more efficient location tracking capability than regular GPS, and improved cellular coverage.

As used herein, the terms "wireless communication system" refers to, without limitation, any system that uses communication stations and a wireless location means for determining positional coordinates such as Global Positioning Radio Service (GPRS).

As used herein, the term "network" refers to, without limitation, any telecommunications network, data network, or Voice Over IP (VOIP) network, satellite, radio, microwave, millimeter-wave, RF wireless, RF cable, optical, and networking protocols (such as IEEE 802.11g), transmission media, and communications connections any combinations thereof.

As used herein, the term "server" refers to, without limitation, any computer element that stores or transfers data, information, or computer applications between one or more computer devices, mobile phones, laptop computers, user computer terminal, or the like, utilizing a network.

As used herein, the term "module" refers to, without limitation, any software sequence or hardware configuration, executable code, XML programming language code, a software code sequence, software program, software executable code, firmware, hardware unit, or the like.

Overview

In one salient feature, the present invention discloses a location tracking method and system, to provide a web interface to display location information associated with tracking devices, back-end systems, and to direct monitoring, displaying, and calculating, inter alia, location coordinates of a tracking device. In one embodiment, the system generates a personalized user profile to organize, control, and store location of one or more tracking devices associated with one or more groups of objects or individuals. The personalized user profile may include one or more user selectable icons (or upload picture (e.g., JPEG or GIF)) icons to monitor on a map display. Upon successful user logon authentication, the system performs a status check and generates one or more alert messages associated with one or more groups of tracking devices to display on a location management dashboard module. A location management dashboard module depicts a listing of one or more groups of tracking devices capable of a user monitoring or requesting monitoring information. One or more wizard menus prompts a user to enter or update personal information, generate or update entries a contact book, and request information associated with past or current status of one or more groups of tracking devices. In another embodiment, if location coordinates of a tracking device (in one or more groups) violates one or more rules defined by a subscriber of the system, the subscriber (or a designated guardian or representative or individuals in a contact book) may be notified through, for example, wireless telephone, plain old telephone system (POTS), Internet, text message, email, vibration, sound, voice, or the like.

Broadly, the present invention generally provides a system and method for monitoring, locating and tracking an individual or an object. The system produced according to the present invention may find beneficial use for locating and tracking people, such as missing, lost, or abducted persons, Alzheimer's syndrome patients, or mentally ill persons. The system may also be useful for locating and tracking animals. Additionally, objects, such as vehicles, goods, and merchandise may be located and tracked with the system produced by the present invention. Although the following discussion may use lost or abducted child as an exemplary demonstration, it is to be understood that this discussion is not limiting and that the present invention may be used in other suitable applications.

Exemplary Systems

Referring now to FIGS. 1-21 and exemplary embodiments of the tracking and monitoring system of the invention described in detail. It will be appreciated that while described primarily in the context of tracking individuals or objects, at least portions of the apparatus and methods described herein may be used in other applications, for example, without limitation, user personal profiles to monitor components such as transducers, sensors, and electrical and/or optical components as the components pass through an assembly line process.

Moreover, it will be recognized that the present invention may find utility beyond purely tracking and monitoring concerns. For example, the "tracking device" and "user selected coverage zones" described subsequently herein may conceivably be utilized to improve displaying and monitoring applications to achieve increased computational efficiency and accuracy of calculated quantities. The calculated quantities may include object velocity (traveling during an assembly process) to determine which process portions are running efficiently and which portions may require improvements or modifications. Other functions might include monitor and track properties of electronic module assembly (e.g., display of electrical properties and measurement parameters during testing and/or operations before, during, or after wireless module completion, and so forth). Myriad of other functions will be recognized by those of ordinary skill in the art given the present disclosure.

Product Activation

Figure 2D:
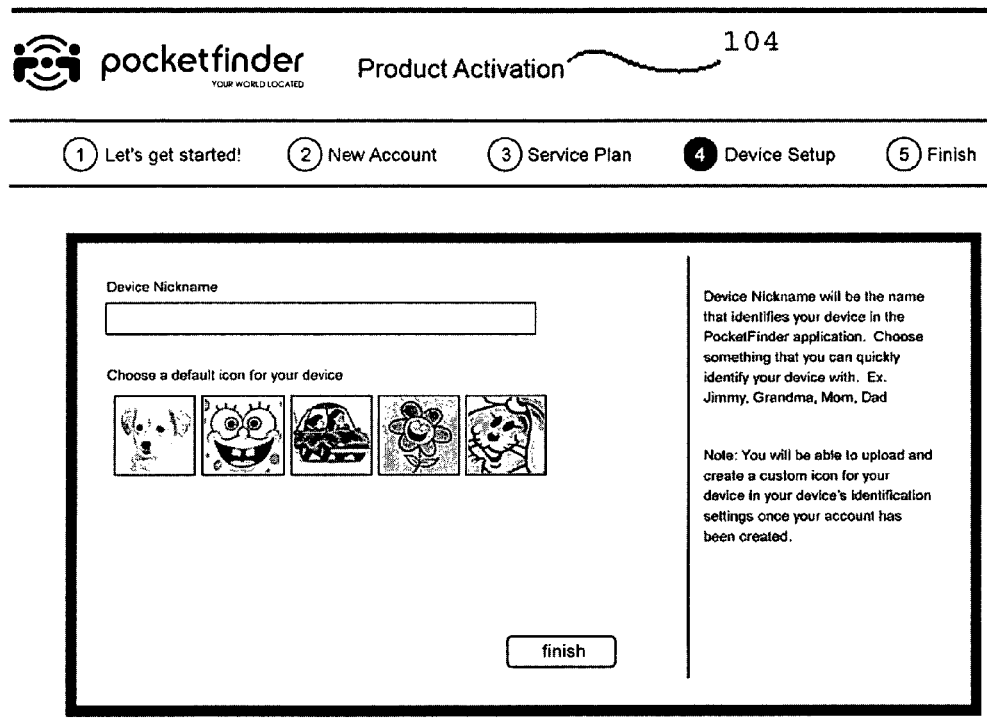
FIG. 2D illustrates a Product Activation Webpage to enter a device nickname in accordance with an embodiment of the present invention.
Figure 2E:
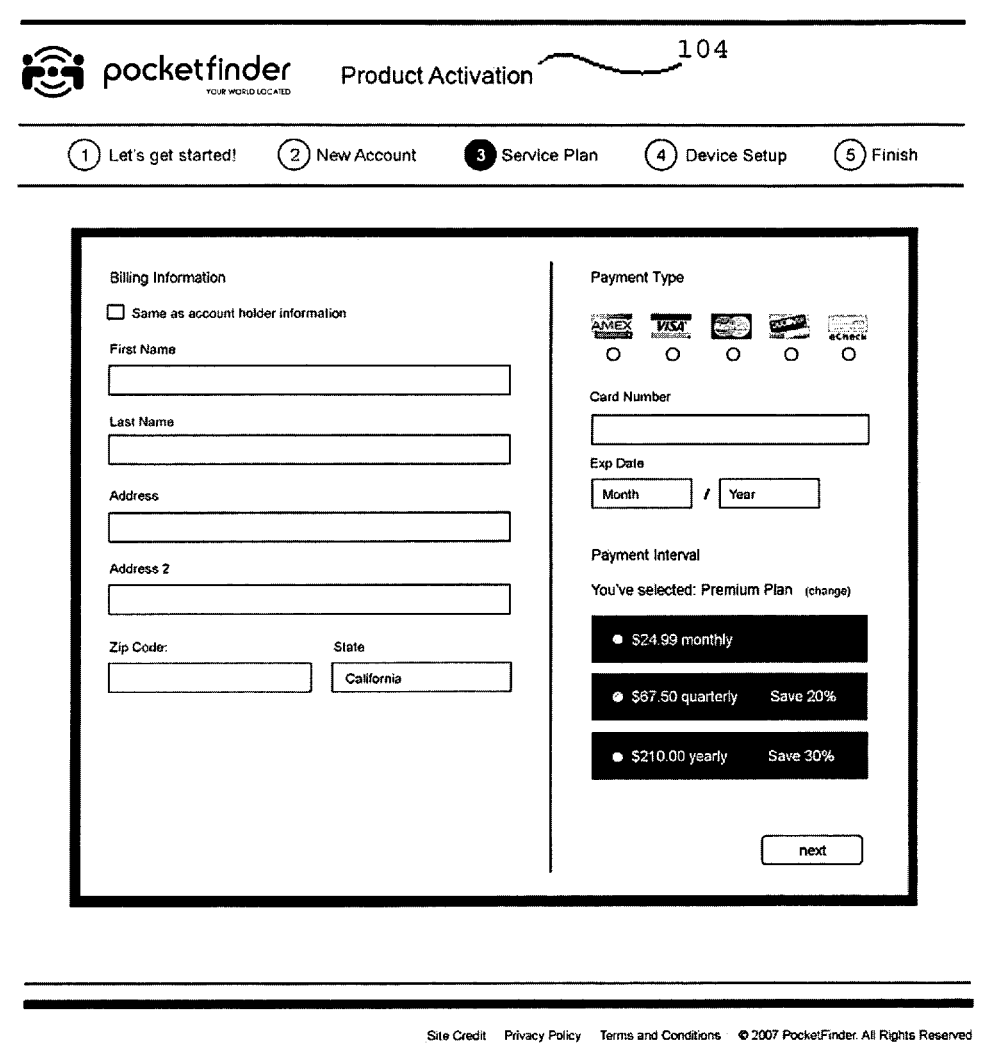
Figure 2F:
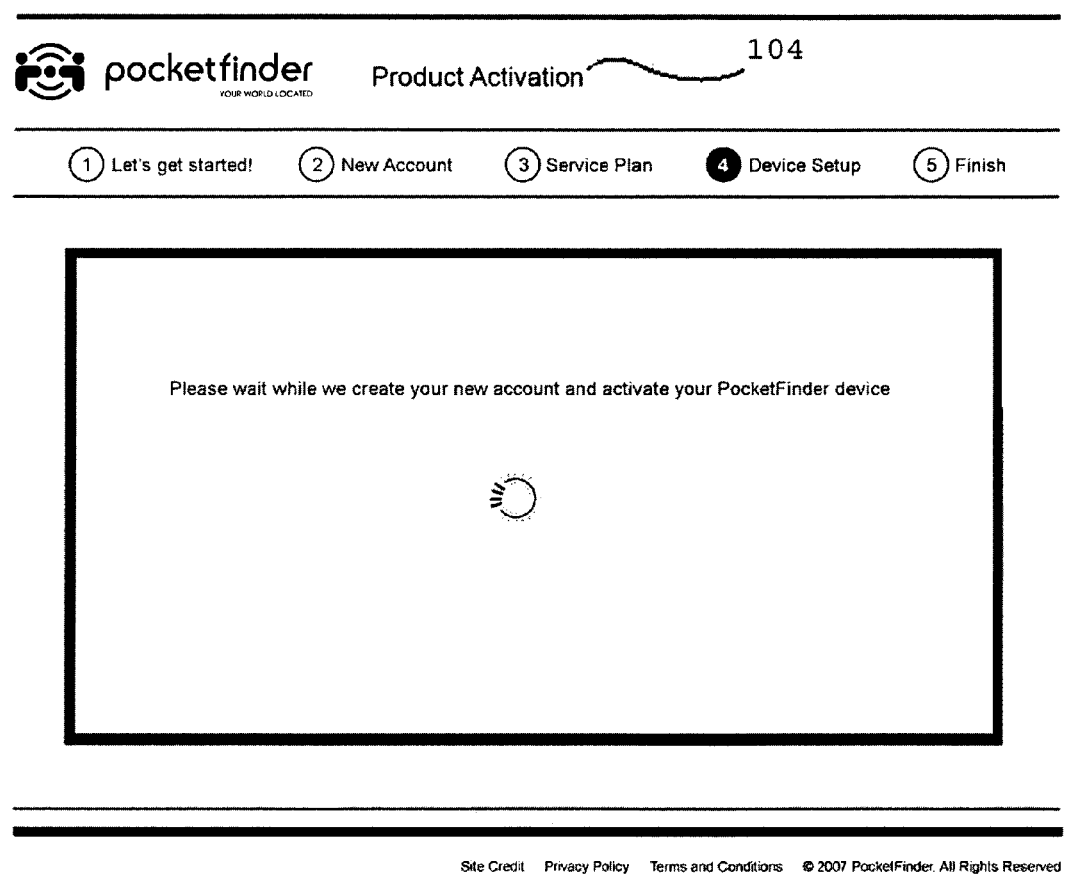
FIG. 2F illustrates a Product Activation Webpage to create a new account and activate your Pocketfinder Device in accordance with an embodiment of the present invention.
Figure 2G:
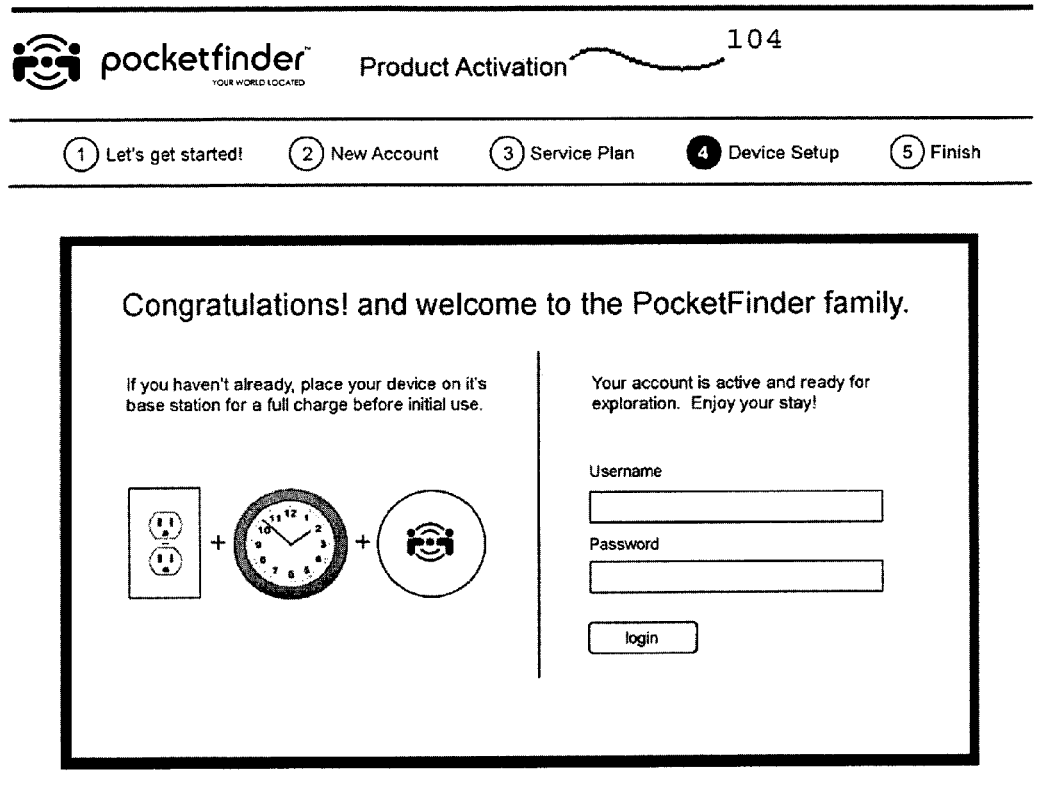
FIG. 2G illustrates a Product Activation Webpage to enter user name and password and to request place your device on its base station for a full charge in accordance with an embodiment of the present invention.

Referring to FIG. 1, a user (e.g., subscriber of the pocketfinder service) accesses a home page of a location and tracking service 100. The pocketfinder service may be activated 104 for a tracking device 102 as well as provide user access to account services that are part of the location and tracking service. Referring to FIG. 2A, device identification code is requested as well as other information including username, password, and current email address. In one embodiment, a subscriber may add an additional device, e.g., new device, to your existing account. Referring to FIG. 2B, New Account wizard menu makes a request for subscriber contact information. In one exemplary embodiment, the New Account wizard menu instructs a subscriber that a mobile phone number, e.g., included as part of the subscriber contact information, will need to be verified in your account settings once you've completed activation before being used as a notification method, e.g., for alert messages of one or more tracking devices. Referring to FIG. 2C, a wizard menu illustrates features, e.g., Premium vs. Standard, as well as monthly price information of the location and tracking service 100. Referring to FIG. 2D, device nickname is requested to allow a subscriber to quickly identify a device, e.g., Jimmy, Grandma, Mom, and Dad. Referring to FIGS. 2E and 2F illustrate billing options and activation wait menu of the location and tracking service 100. Referring to FIG. 2G, a user is requested to place their tracking device 102 on a base station to charge its battery level.

Service Login

Figure 3:
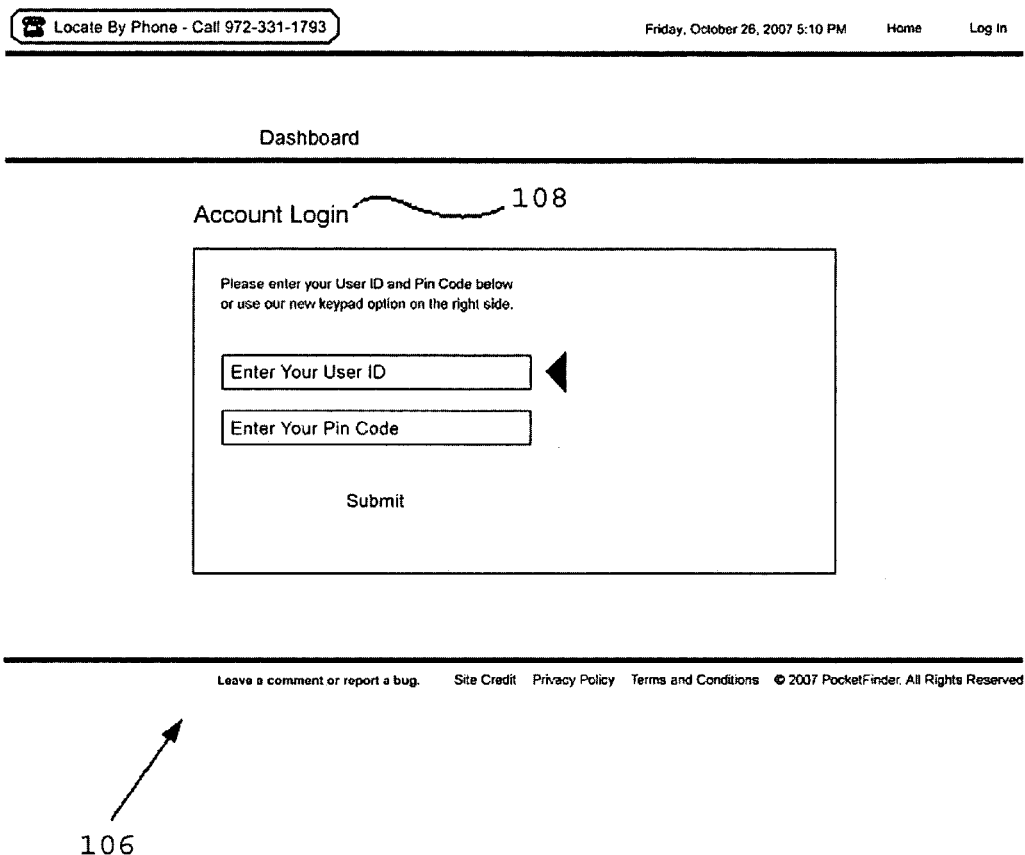
FIG. 3 illustrates an Account Logon Webpage in accordance with an embodiment of the present invention.

Referring to FIG. 3, a user receives access to logon module 106. In one example, logon module 106 includes logon entry display (e.g., account login 108). In one embodiment, the logon entry display accepts numbers and letters (see FIG. 14). In this example, a user enters a name and password (e.g., user id and pin code) into the account login 108. In one variant, anti-key logger technology protects entries including a name and password. In one embodiment, account login 108 on an Internet website utilizes a similar account login on a telephone unit, e.g., mobile communication unit, because both utilize, in one example, the same (or substantially similar) user id and pin code.

My Account

Figure 4:
FIG. 4 illustrates a Help Settings Webpage in accordance with an embodiment of the present invention.
Figure 6:
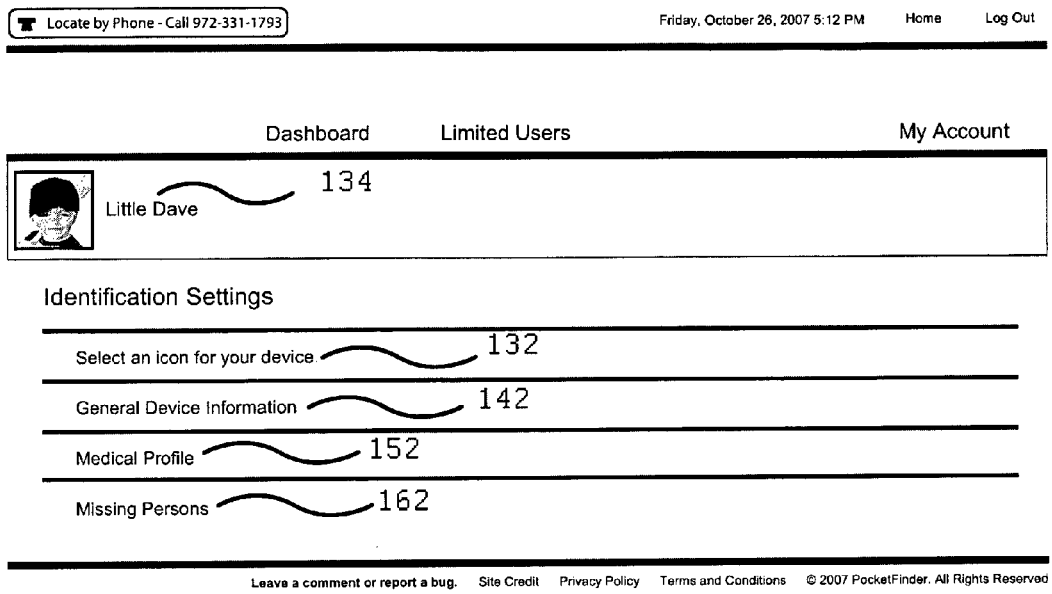
FIG. 6 illustrates an Identification Settings Webpage of a tracking device represented by Icon of Little Dave in accordance with an embodiment of the present invention.
Figure 7:
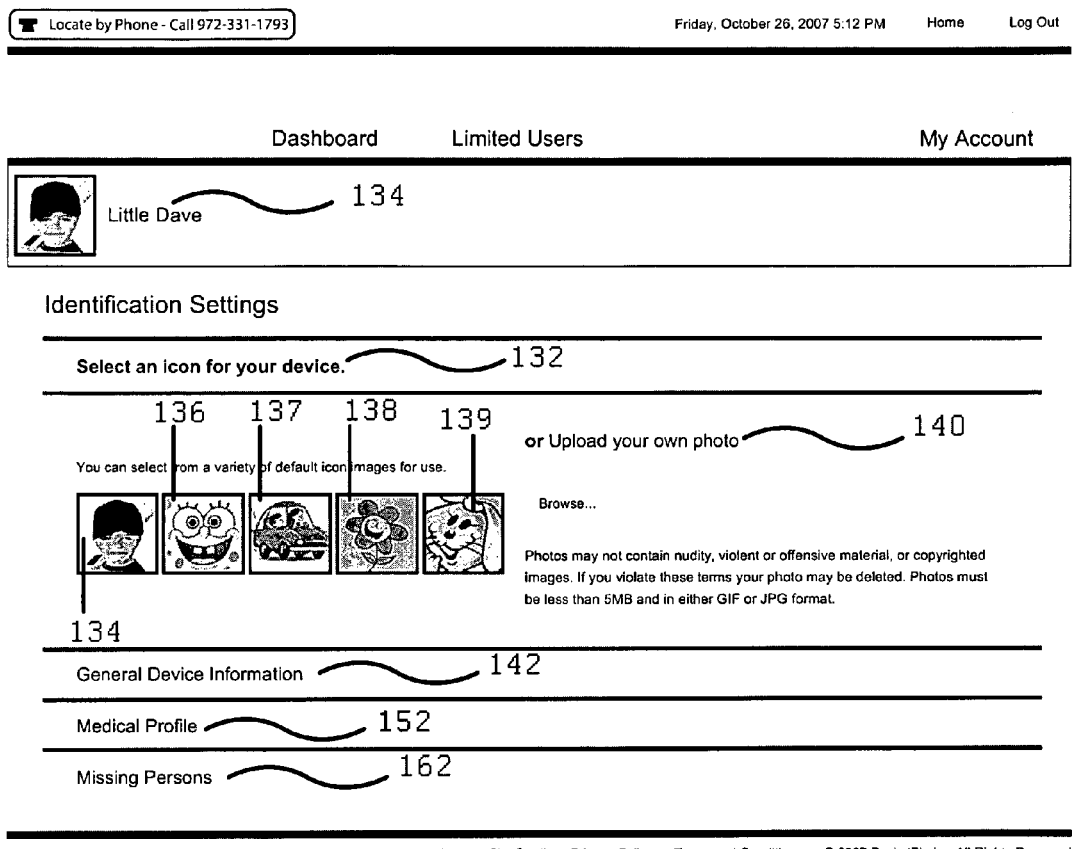
FIG. 7 illustrates an Identification Settings Webpage to select an Icon to represent a Tracking Device in accordance with an embodiment of the present invention.

Referring to FIG. 4, after successful authentication of a user id and pin code, a user accesses account services module (e.g., my account 110). Account services module (e.g., my account 110) generates a user profile (e.g., account settings 112) of building blocks, e.g., elements, to organize user profile contents and structure (e.g., account holder information 114, contact book 116, help settings 118, account billing 120, and cancelling your account 122). The user profile, in one embodiment, requests location information on a tracking device 102. According to one embodiment, mark-up language (XML) constructs account services module 110. Upon authentication of a user id and pin code, a user proceeds to account holder information module 114. Referring to FIG. 5, a user enters identification information (into account holder information module 114), for instance, first name, last name, address 1, email, city, password, home phone number, mobile phone number, zip code, and email address(es). Advantageously, a user may utilize the same user profile (e.g., account settings 112) for location and tracking requests using a telephone or mobile phone or using a computer terminal (and logging on to a pocketfinder webpage). In another embodiment, a user may choose a different user profile responsive to a format or type of wireless or wired device. Available pull down module menus include contact book 116, help settings 118, account billing 120, and cancelling your account 120.

Identification

Figure 9:
FIG. 9 illustrates General Device Information Webpage for Little Dave in accordance with an embodiment of the present invention.

Referring to FIGS. 6-10, a user provides values for device identification module 127. In device identification module 127, a user, for instance, chooses one of a list of icons to represent one or more tracking devices associated with an individual, object, or animal. In one example, the list of icons includes default icon images (e.g., 134, 136, 137, 138, and 139) or (in one variant) a personnel icon, e.g., a photo in JPEG or PDF format file 140 may be uploaded. In one embodiment, device specific information may be entered. For instance, device specific information for Little Dave 134 may include medical profile module 152 (as shown in FIG. 8), including: birthday, blood type, allergic medications, medical conditions, and physician's name and phone number. To further personalize tracking device parameters in device identification module 127, general device information 142 is inputted for one or more tracking device in one or more groups including: device nickname, first name, and last name (as shown in FIG. 9).

Contact Book

Referring to FIG. 11, a user enters values into contact book module 116. The values define contact information, e.g., first name, last name, home phone number, mobile number, and email address. To verify entered values, a return email, for example, generates automatically to request value validation (e.g., verify 166) of entries input into contact book module 116.

Limited Access

Referring to FIG. 12, a wizard menu provides user access to enter information for limited access users module 170. More specifically, temporary or limited access to tracking device particulars may be extended on a limited user basis. In one embodiment, the limited user basis may be assigned on a per device basis. For instance, a limited user basis may include assigning a list of limited access users to one or more of the following devices (check-box icon display menus 172, 174 . . . the newly created user will be able to see the location of the following checked devices. Don't worry access can always be modified anytime by you).

Location Management Dashboard

Figure 10:
FIG. 10 illustrates a Device Speed Limit Webpage for Little Dave in accordance with an embodiment of the present invention.
Figure 13:
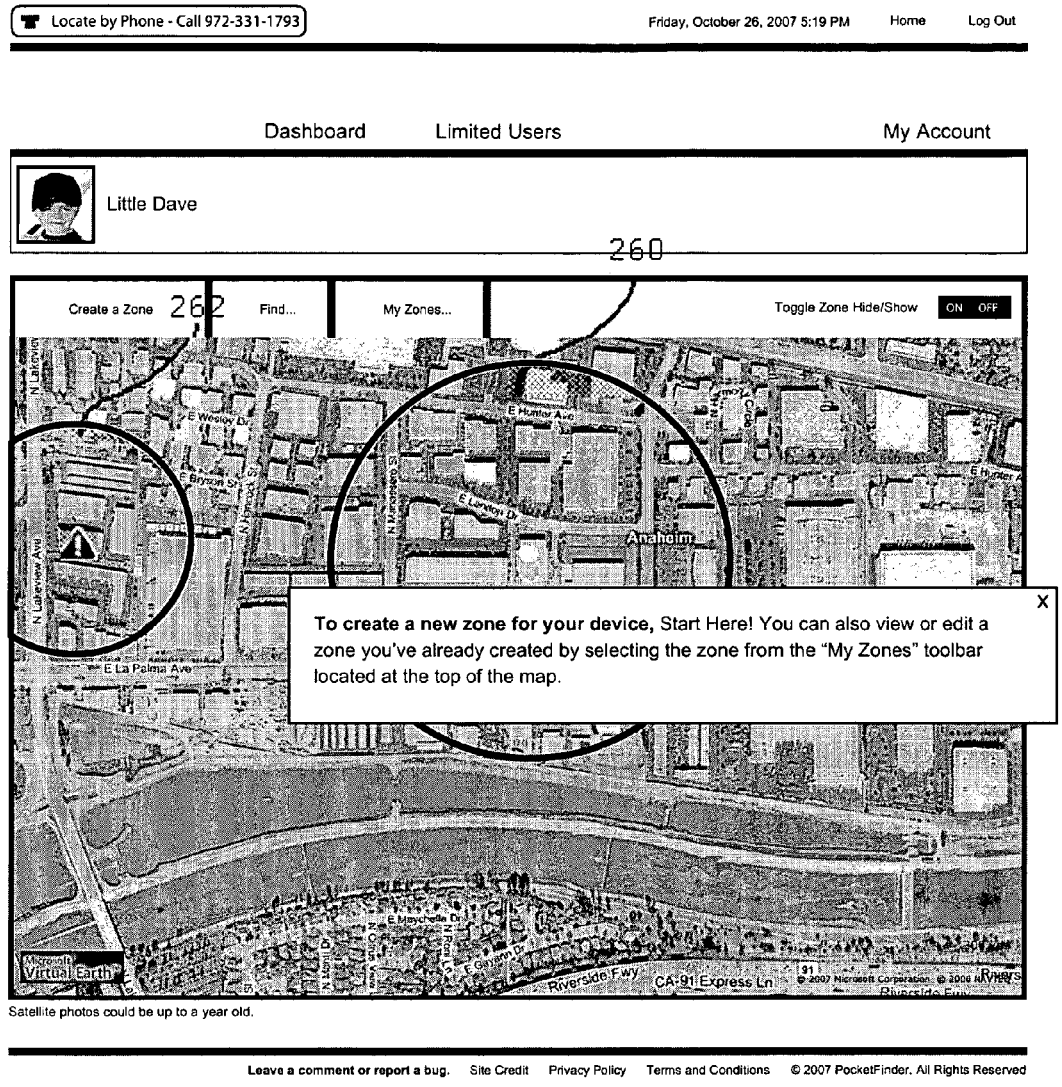
FIG. 13 illustrates a Map having User Selected Coverage Zones in accordance with an embodiment of the present invention.
Figure 14:
FIG. 14 illustrates a Map for creating User Selected Coverage Zones in accordance with an embodiment of the present invention.
Figure 15:
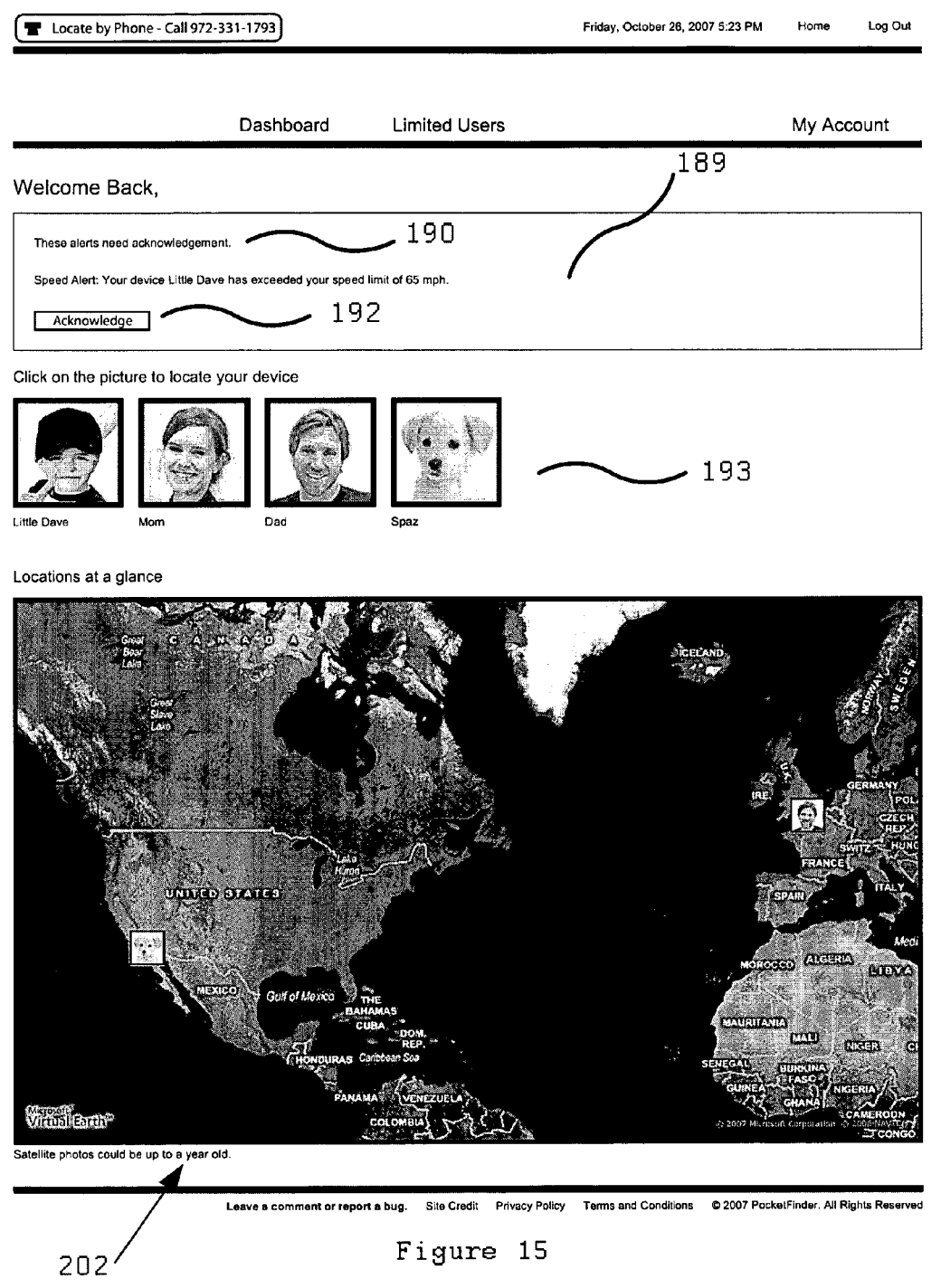

Referring to FIGS. 13-19, representative menus are depicted for location management dashboard module 189. FIG. 12 illustrates two user defined coverage zones 262, 260 for Little Dave. FIG. 14 illustrates an overall street map to locate Little Dave. FIG. 15 depicts location management dashboard module 189 having a family account module 193. The family account module 193 includes family members (e.g., Little Dave, Mom, Dad, and Spaz). In one embodiment, the system prompts a subscriber (user) of alerts (e.g., alert messages) that need acknowledgement (e.g., acknowledge 192). The alert messages (e.g., speed alert 190) include, for example, a breach condition (e.g., defined by a user or a system administrator such as a maximum speed limit or distance from a freeway entrance or exit) associated with one or more icons, dangerous locations, or dangerous surroundings proximal to an individual or object having a tracking device 102 (e.g., Little Dave, Mom, Dad, and Spaz) as shown in FIG. 10.

Alert

In one embodiment, upon successful acknowledgement of a subscriber log on, alert messages (see FIG. 15) automatically populate the location management dashboard 189. Alert messages may be selected or inputted by, for example, a subscriber or system administrator and may include one or more warnings (or illustrative warning messages that may increase/decrease in intensity) to indicate a dangerous condition, a security breach, or the like, for a tracking device, such as tracking device 102. In one embodiment, an alert message generates when a tracking device (in the group) indicates a breach condition, e.g., battery is disconnected from a tracking device. In one embodiment, an alert message generates upon detection of a cut wire in a tracking device. In one variant, an alert message generates when a vehicle (including an individual or object having a tracking device) exceeds a specified speed limit (see FIG. 15). In one embodiment, when a battery temperature exceeds a specified temperature, the system communicates a signal to the tracking device to temporarily power down for a specified cooling period. In another embodiment, upon battery charge level falling below a specified level, an alert message communicates to shut down or reduce power consumption of a tracking device. In one variant of this embodiment, an individual having a tracking device receives, in one example, an indication, e.g., an audio sound or voice command, to locate a power charging unit. In another embodiment, a designated individual in contact book 116 may be contacted upon detection of a breach condition, e.g., violation of a user defined system policy, by a tracking device. In another embodiment, the pocketfinder service 100 may send, for example, communicate an audible or vibrate signal to the tracking device to locate a base unit responsive to a battery charge level, e.g., and provide signaling to a tracking device to enter a designated battery charging mode, such as a quick charge and/or trickle charge.

Mapping

Figure 16:
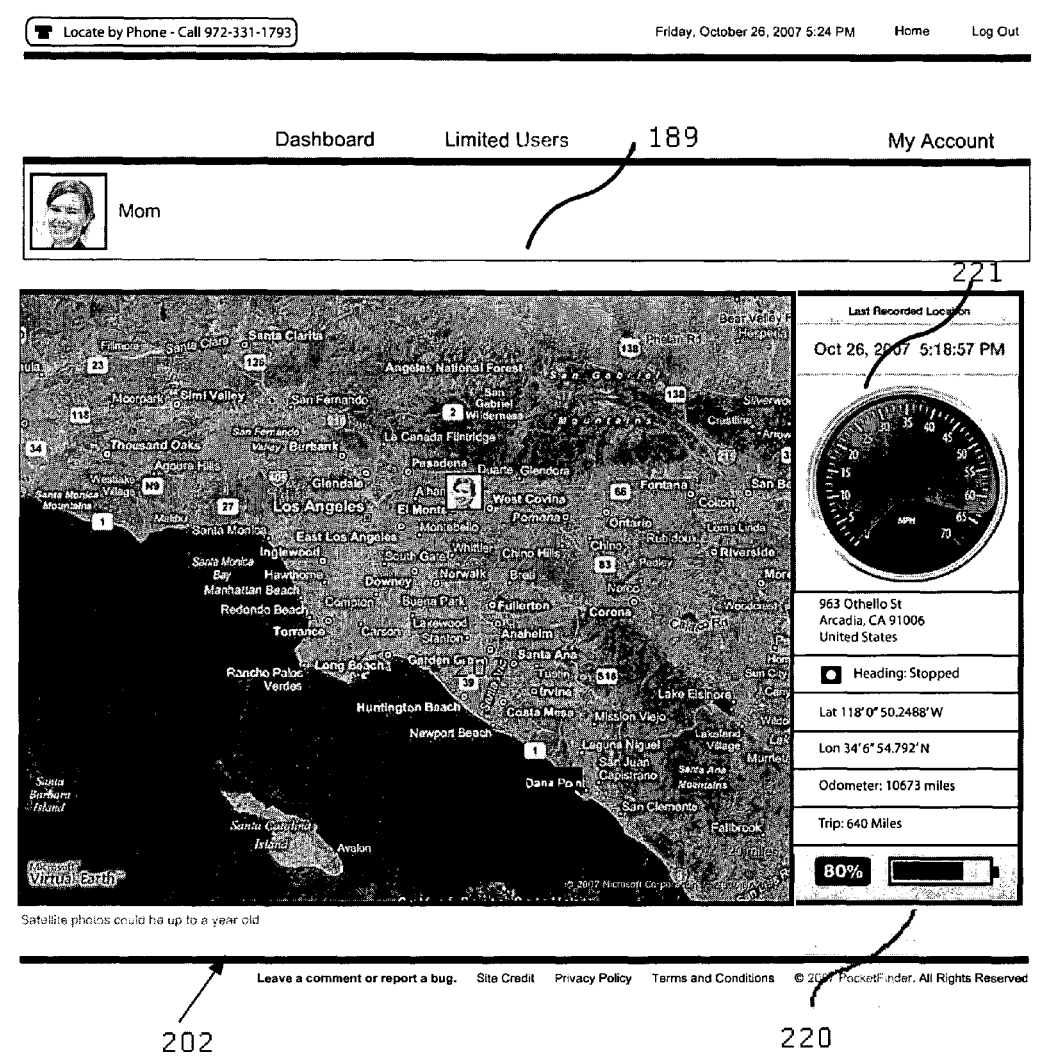
Figure 17:
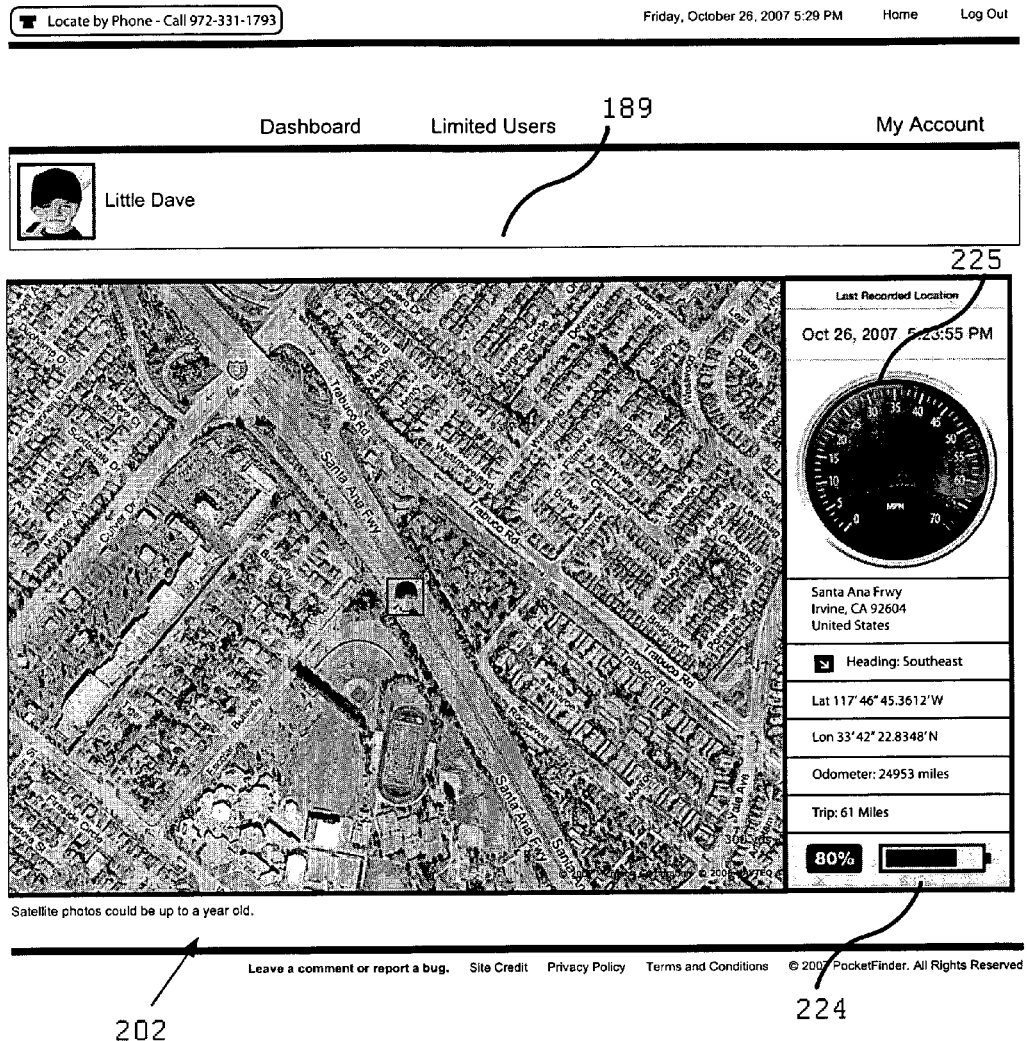
FIG. 17 illustrates a Location Management Dashboard Webpage associated with Little Dave including: Location Coordinates, Battery Management Module, and Velocity Display Module in accordance with an embodiment of the present invention.

Referring to FIG. 15, a mapping module 202 depicts, for example, location of an object (e.g., Spaz) or an individual (e.g., Dad), using the pocketfinder device. Referring to FIGS. 16-17, a mapping module 202 indicates proximal to a mapping area representative icons, e.g., velocity indication devices (e.g., speedometers 221, 225) to indicate instantaneous speed of an individual (e.g., Mom or Little Dave equipped with a tracking device, such as tracking device 102). Other information provided with the mapping area may include location coordinates, e.g., latitude, longitude, odometer reading, and trip miles.

Referring to FIG. 10, a user selects a device speed setting (e.g., set you maximum speed: 65) 180 for Little Dave. An alert message 190 generates, for instance as shown in FIG. 15, if Little Dave exceeds a speed limit of 65 miles per hour (e.g., a breach condition). The alert message 190 may require one or more notification methods including: email 182 (e.g., Mike@actti.com), short message service (SMS) 184, or voice 186. In one variant, the alert message 190 may be provided to one or more persons in, for instance, information contained in contact book 116, in an event that an acknowledgement is not received (e.g., within a specified interval) by a first alert message recipient, e.g., Mike@actti.com.

In one user defined situation, an alert message may be generated when Little Dave exceeds a specified distance from a specified set of location coordinates. Furthermore, individuals in contact book 116 may be notified in accordance with, for instance, recognition of a breach condition. In one embodiment, the breach condition may be in accordance with one or more user defined criteria. In another embodiment, a breach condition may result from an occurrence of one or more (e.g., user) specified events.

For instance, the user defined criteria may include: notification to an individual in contact book 116 having a closest stored address to a last known or current address of the tracking device 102 requesting, for instance, a positive acknowledgement to an outgoing alert message, notification based on oldest to youngest family member, last contacted individual known available from contact book 116, or the like. The happening of one or more specified events may include notification of another individual in the contact book 116 upon multiple failed requests for a first recipient to acknowledge receipt of an alert message.

In contrast to many conventional location and tracking devices, such as RFID, a tracking device of the present invention advantageously provides capability of nationwide and global location coordinates monitoring and tracking of persons or objects. Advantageously, the present invention being a multi-format location and tracking service may utilize a multitude of devices (e.g., desktop computer, laptop computer, land-line phone, mobile phone, personal digital assistant, or the like, because it does not utilize a specialized data format; thus, this service does not require a specialized data reader, e.g., RFID reader, to read data. Furthermore, unlike other conventional identification systems, the service provided by the present invention does not require a tracking device, such as tracking device 102, being physically constrained within a specified distance to be read by a reader, e.g., a RFID reader.

Furthermore, the service of the present invention being in XML format provides a universal format so location coordinates may be readily communicated (e.g., via Bluetooth) between various computer and personal assistant formats such as a laptop computer and a wireless device, such as a mobile phone. Consequently, the service depicted by the present invention either semi-automatically or automatically adjusts to a software platform or Internet Browser including Safari 3.5 software. In addition, an identification code may be regenerated for a tracking device (on a periodic basis or upon occurrence of a security breach as discussed previously incorporated by reference U.S. patent application Ser. No. 11/753, 979 filed on May 25, 2007, whereas RFID devices have a security code that is preprogrammed and (once cracked), all RFID devices having the security code are vulnerable to unauthorized detection.

To understand methodology of the service 100 (e.g., location and tracking device interface) of the present invention, an exemplary example of its use is discussed supra. In this example, a user provides a request signal to obtain location coordinates of a first tracking device. The first tracking device provides a first reply signal that comprises a first identification code to identify the tracking device. The location coordinates are displayed of the first tracking device to the user in response to the request signal. A second tracking device of one or more groups of tracking devices has a second transceiver to receive the first reply signal, compare the first identification code to a stored identification code, and communicate to a monitoring station a second reply signal. The second reply signal comprises the location coordinates of the first tracking device in part responsive to verification of the first identification code.

Coverage Zone

Figure 18:
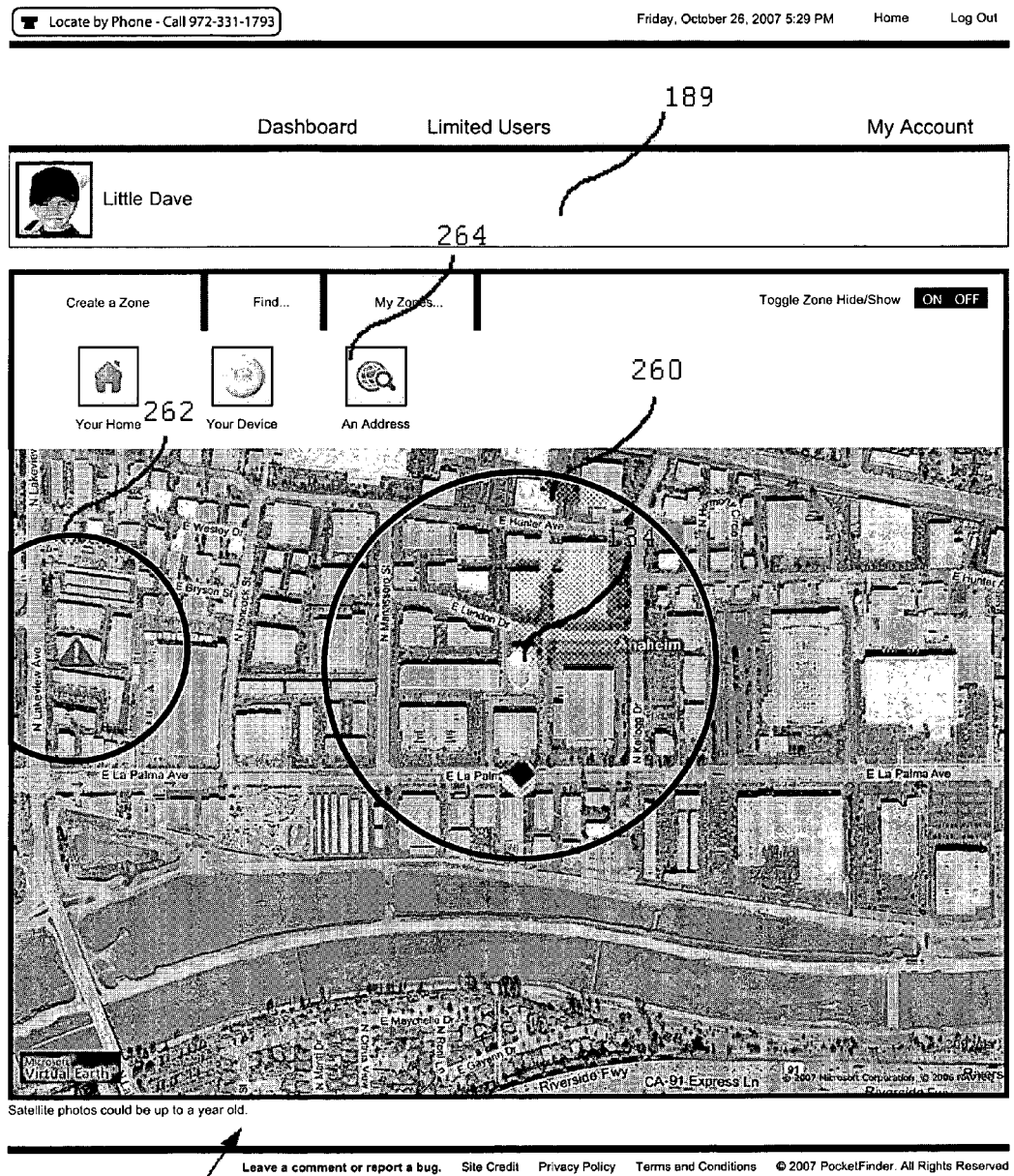
FIG. 18 illustrates a Location Management Dashboard Webpage including User Selected Coverage Zones associated with Little Dave and selectable user menus to obtain location information relative to Your Home, Your Device, and An Address in accordance with an embodiment of the present invention.
Figure 19:
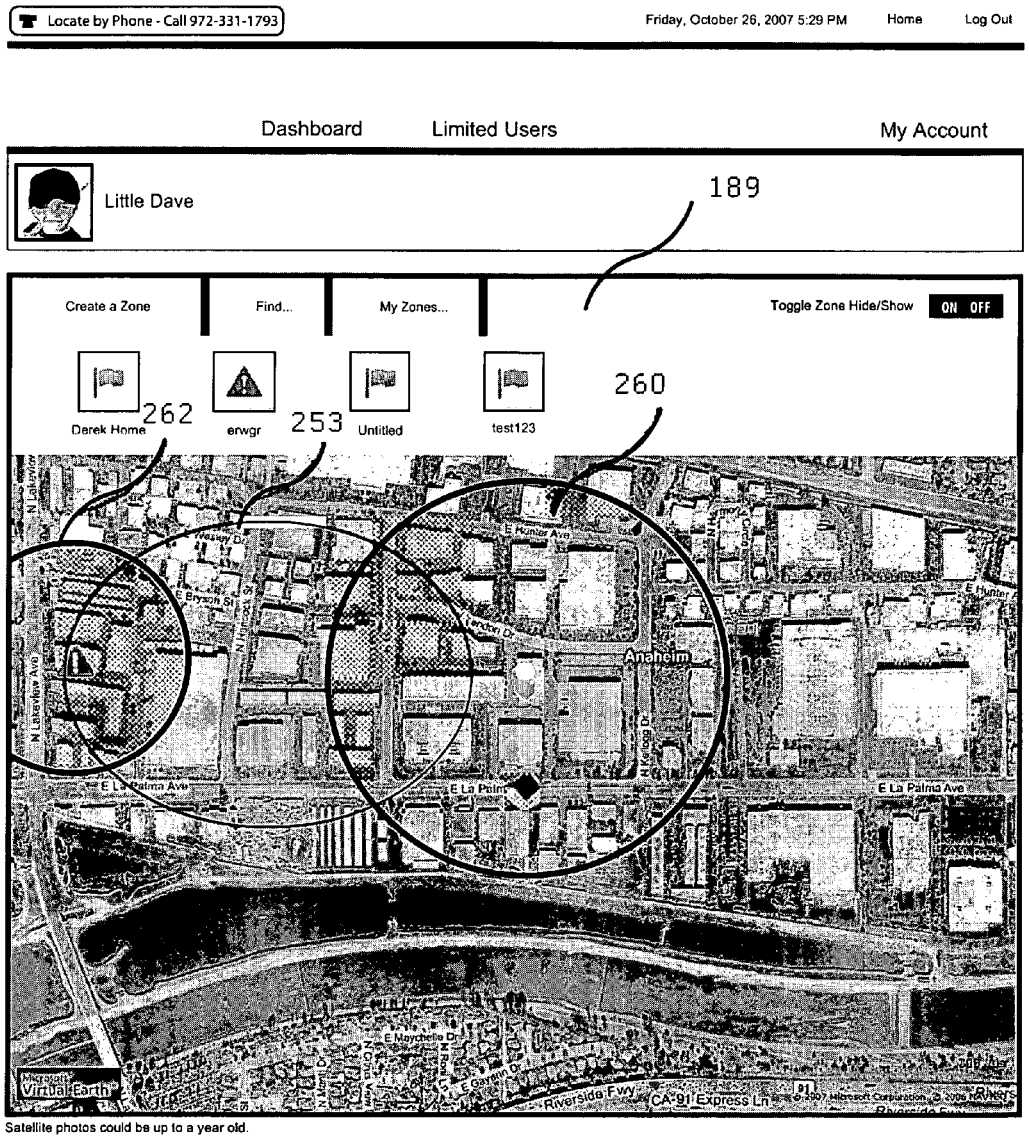
FIG. 19 illustrates a Location Management Dashboard Webpage including User Overlapping Coverage Zones associated with Little Dave and selectable user menus to obtain location information relative to Derek Home, enwgr, Untitled, and test 123 in accordance with an embodiment of the present invention.
Figure 22:
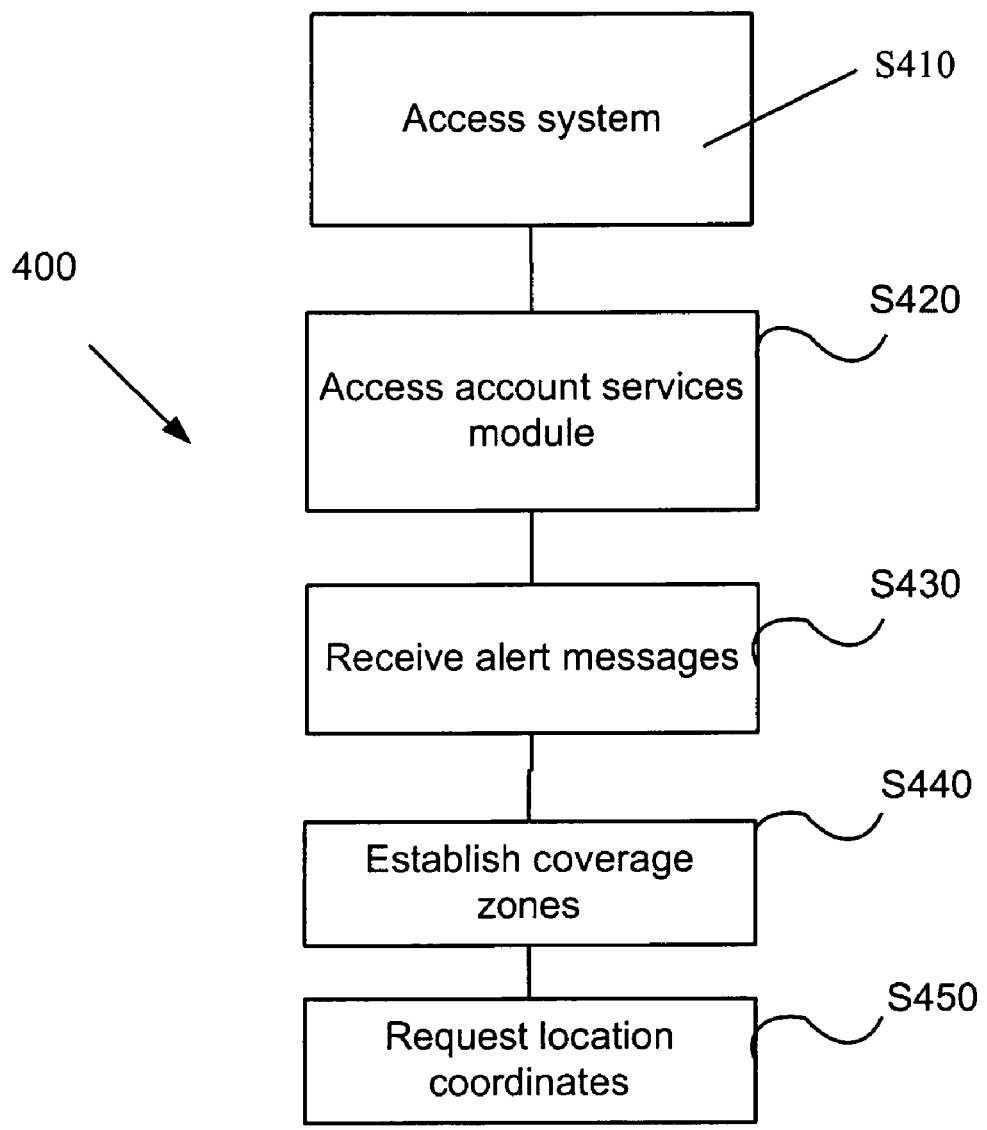
FIG. 22 illustrates a Flow Chart to create a Location and Tracking Service Webpage in accordance with an embodiment of the present invention.

Referring to FIGS. 18-19, user provides entries using a keyboard and/or mouse to generate a coverage zone module 258. The entries may include monitor and zone attributes, for instance, on a satellite map. In this example, the map depicts location coordinates of Little Dave 134 as well as relative physical location to other landmarks (e.g., your home) or street addresses on the map (e.g., E. La Palma Ave). In this same embodiment, the one or more management zones (e.g., safe zone 260 and unsafe zone 262) set safety and danger attributes of the service 100. These safety and danger attributes are utilized to notify individuals in contact book 116 relative to a user selectable notification process. A user selectable notification process may include transmission (and return receipt or acknowledgement) by one or more telecommunication services, e.g., SMS text messaging, cell phone (IVR), landline phone, email, and IM (Instant Messaging) as shown in FIG. 10.

With regards to zones of coverage (e.g., unsafe zone 262, safe zone 260), a user modifies or deletes one or more of these at one or more periodic (in one variant, one or more a periodic) intervals. In one variant, zones of coverage may be automatically generated and deleted. In one embodiment, one or more overlapping user defined coverage zones (e.g., created by coverage zone 253 that overlaps zones 260 and 262 shown in FIG. 19) may designate, for instance, a relative distance and/or region, for instance, a safe zone 260 and an unsafe zone 262. In one variant, a relative distance may be communicated to a user of a proximal location of a tracking device 102 to a perimeter of a safe zone 260 or unsafe zone 262. In one embodiment, a relative location coordinate error margin between the safety zone 260 and the unsafe zone 262 prevents a false alert being generated and communicated to a user.

Referring to FIG. 18, the coverage zone module 258 may utilize a smart interactive service module 264. A smart interactive service module 264 allows a user to utilize quick search features to set-up coverage zones. For instance, smart interactive service module 264 includes quick physical address lookup, quick home address locate, or quick locate unit options, e.g., where a stored or partially stored portion of these values provide improved, more efficient access to desired location information. A coverage map automatically tracks positional coordinates of a tracking device 102. In particular, a coverage map automatically repositions tracking device location coordinates, e.g., centrally locates for viewing, in response to a user's inputs utilizing quick look-up features, e.g., such as quick physical address lookup).

Missing Persons Report

Upon failure to locate Little Dave (cannot be found using the pocketfinder service), a missing person's report 278 is automatically prepared (see FIG. 20). The report includes, for example, print Missing Flyer 280 (including Little Dave's physical description as shown in FIG. 21). The missing person's report 278 may be submitted to authorities, e.g., Police Department, or individuals in contact book 116 in accordance with instructions provided by a user, e.g., closest individual to a last known address of Little Dave, oldest family member or other user defined criteria previously defined in above embodiments.

Battery Conservation

If a tracking device 102 looses contact with a monitoring station, a battery management module (e.g., represented graphically by battery icons 220 (for Mom) and 240 (for Little Dave) in FIGS. 16, 17, respectively), in one embodiment, places the tracking device in a low power mode to conserve power, e.g., during a mobile communication dead zone or no transmission zone. In one variant, the battery management module may maintain a lower power mode of a battery of a specified tracking device (e.g., Mom or Little Dave) until a later specified interval (upon which mobile communication may be possible) to conserve battery life. In one example, a user commands other pocketfinder devices, e.g., tracking devices such as Mom or Dad, to communicate last or current location coordinate information of a lost pocketfinder device, e.g., Spaz or Little Dave. In another embodiment, a user may turn-off power of a tracking device suspected of being monitored by unauthorized individuals (e.g., initiate tracking device cloaking option).

In another embodiment, an expanded cellular network is created by pocketfinder devices having proximate location coordinates, e.g., nearby devices generate relative tracking location coordinates between each other or a central monitoring station to increase a monitoring range of a tracking device. Consequently, in the expanded cellular network, a momentary loss of communication, a communication dead zone, between one and more tracking device has the capability of not thwarting monitoring of the tracking device.

In another embodiment, upon a user loosing connectivity with a tracking device, the user waits until another specified period to power-on (e.g., provide operational power to the tracking device) before monitoring; thus, the tracking device battery power is conserved when occupying a communication dead zone. In another embodiment, the tracking device bursts location coordinates (at specified intervals) to conserve tracking device battery life (allowing the tracking device to poweroff or move to a low-power level). In another embodiment, a safety zone of the tracking device indicates when a tracking device is detected proximal to an area of a known criminal or sex offender.

Exemplary Methods

Referring to FIG. 21, a flow chart (400) illustrates generation of a personalized user profile of one embodiment of the present invention. In step 410, a user accesses the location and tracking system 100. In step 420, the user accesses an account services module 110. In step 430, the user receives alert messages of tracking devices in a group 193. In steps 440 and 445, the user establishes coverage zones (e.g., 253, 260, and 262) for tracking devices in the group 193. In step 450, the user request location coordinates of one or more tracking devices in the group 193.

It is noted that many variations of the methods described above may be utilized consistent with the present invention. Specifically, certain steps are optional and may be performed or deleted as desired. Similarly, other steps (such as additional data sampling, processing, filtration, calibration, or mathematical analysis for example) may be added to the foregoing embodiments. Additionally, the order of performance of certain steps (e.g., steps 410-450) may be permuted, or performed in parallel (or series) if desired. Hence, the foregoing embodiments are merely illustrative of the broader methods of the invention disclosed herein.

While the above detailed description has shown, described, and pointed out novel features of the invention as applied to various embodiments, it will be understood that various omissions, substitutions and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. An expanded cellular communication system comprising:
   one or more tracking devices;
   a display device for displaying a user interface;
   a server coupled to the display device, the server having stored computer-executable instructions that, when executed at the server, configure the server to implement:
   a user dashboard interface module configured to display a user dashboard interface on the display device and to monitor a group of the tracking devices in accordance with user selected coverage zones; wherein the user selected coverage zones comprise coverage zones associated with one or more mapping areas determined to be at least one of a safe zone and unsafe zone;
   an alert module configured to generate an alert message in accordance with detecting a breach condition of one or more of the user selected coverage zones;
   an identification module configured to be user selectable to remotely set control variables of an individual or an object associated with a tracking device of the group of tracking devices to partially establish conditions determining if the breach condition of one or more of the user selected coverage zones occurred; and
   a battery management module arranged to set the tracking device in a low power mode for a specified duration in response to a loss of contact with the tracking device.

2. The system of claim 1, wherein the alert module provides the alert message upon a user successfully logon to the user dashboard interface module.

3. The system of claim 1, further comprising an icon module that provides graphical representations of the group of tracking devices; wherein the icon module provides capability of selecting the tracking device to monitor and provide location coordinate information of the tracking device by another device of the group of tracking devices upon detection of no response during a specified period by a monitoring system of the location coordinates of the tracking device.

4. The system of claim 1, further comprising a battery management module capable of powering on the tracking device for a specified period in response, to a monitoring station previously powering-down the tracking device in response to the monitoring system not detecting the location coordinates of the tracking device.

5. A system comprising:
   a mapping display;
   a server coupled to the mapping display, the server storing the computer-executable instructions that, when executed on the server. configure the server to implement:
   a coverage zone module to monitor location coordinates of a tracking device, the module comprising at least two user selectable coverage zones to locate the tracking device;
   a user wizard interface to draw the at least two user selectable zones on the mapping display; and
   an alert system to automatically poll location coordinates of the tracking device at designated periods and to provide an alert in response to a proximal distance of the location coordinates to the at least two user selectable zones; wherein the alert communicates a user defined message responsive to the proximal distance of the location coordinates to the at least two user selectable coverage zones,
   the alert system arranged to notify a contact having a closest address to at least one of a last known address or a current address of the tracking device when the tracking device exceeds a reset distance from a specified set of location coordinates; and a battery management module arranged to set the tracking device in a low power mode for a specified duration in response to a loss of contact with the tracking device.

6. The system of claim 5, wherein the module further provides relative positional measurement of an icon representation of the tracking device along a perimeter of the at least two user selectable coverage zones.

7. The, system of claim 5, wherein the alert system communicates information between a battery management module and the coverage zone module in response to a battery management module detection of a low battery condition of the tracking device, 8. The system of claim 5, wherein the at least two user selectable coverage zones are programmable by a user and in part responsive to updates in a database with regards to location coordinates of at least one of criminals and sexual predators.

9. The system of claim 5, further comprising an acknowledgement system to periodically check if a recipient designated in a contact book successfully communicates an acknowledgement of the alert and to resend the alert to the recipient designed in the contact book upon detection of no acknowledgment of the alert.

10. The system of claim 9, wherein the acknowledgement system chooses another recipient from the contact book in response to detection of no acknowledgement of the alert by the recipient designated in the contact book.

11. The system of claim 10, wherein the acknowledgement system chooses another recipient from the contact book in an order designated by at least one of the user and a system administrator of a remotely located monitoring control station, and wherein the module graphically depicts as one or more icons indicative of directional information of the tracking device, and one or more battery level icons associated with the tracking device indicative of a battery charge level, 12. The system of claim 5, further comprising a smart interactive service to reduce a number of keystrokes required to setup or modify attributes associated with the at least two user selectable coverage zones.

13. The system of claim 5, further comprising an acknowledgement system to automatically alert a user of status information of the tracking device upon successful logon, 14. The system of claim 5, wherein the at least user selectable coverage zones comprise at least two overlapping coverage regions of at least one of a safety zone and at east one of danger zone; and wherein a relative location coordinate error margin between the safety zone and the danger zone prevents a false alert being generated and communicated to a user, 15. The system of claim 5, wherein the at least two user selectable coverage zones comprise graphical icons of tracking devices of a group of tracking devices that a user has monitoring permission; and wherein at least one tracking device in the at least two user selectable coverage zones being responsive to communicate its location coordinates and relative location coordinates from the tracking device to a location monitoring station in response to the tracking device failing to respond during a specified interval to multiple, communicated location coordinate requests.

16. A system comprising:
a display device;
a server coupled to the display device, the server storing server-executable instructions that, when executed on the server, configure the server to implement:
a location and tracking webpage interface displayed on the displayed device and comprising a management menu to provide graphical icons of objects or individuals associated with a tracking device; a zone menu: an alert menu to provide alert information associated with one or more coverage zones selected utilizing a wizard menu; wherein the wizard menu comprises part of the zone menu; and wherein the alert information is responsive to a location request; and a battery management menu to adjust a power level of the tracking device responsive to detection or no detection of communication of location coordinates in response to the location request; wherein the power level of the tracking device transitions to a low power level upon multiple failed location requests for the location coordinates and transitions to an operational power level within a specified period subsequent to transitioning to the low power level.

17. The system of claim 16, wherein the zone menu comprises user selectable overlapping coverage zones to provide a mapping intersection area of safe and unsafe zones and a graphical velocity indicator to indicate speed and directional information of the tracking device relative to landmarks or street addresses on a mapping area.

18. The system of claim 16, wherein the zone menu comprises overlapping user coverage zones; and wherein the alert menu provides mapping area specific alert messages being at least partially responsive to a proximal location of the tracking device relative to the overlapping user coverage zones and a last measured battery level of the tracking device relative to distance from a battery charging station.

19. The system of claim 16, wherein the alert menu comprises an alert message responsive to a last measured battery power level and a relative distance of the tracking device to a battery charging station.

20. The system of claim 16, wherein the alert menu comprises an alert message responsive to a current battery power level of the tracking device and a distance of the tracking device to an open or currently available battery charging station.

21. The system of claim 16, wherein the alert menu comprises an alert message responsive to a relative location of the tracking device to at least one of a group of tracking devices and in part responsive to a distance of the tracking device to a perimeter of an unsafe coverage area and a safe coverage area, a last measured battery power level, and distance to a battery charging station.

22. The system of claim 16, further comprising a contact book menu comprising a list of individuals to contact in response to detecting a security breach of the tracking device, the list of individuals comprises one or more recipients to contact in accordance of a shortest distance between a recipient contact book address and at least one of a last known address or current address of the tracking device upon detecting a failure of a first selected recipient to provide acknowledgement of receipt within a specified period of at least one of multiple transmissions of an alert message.

* * * * *